United States Patent
Littman et al.

(10) Patent No.: US 10,100,113 B2
(45) Date of Patent: Oct. 16, 2018

(54) MATERNAL TH17 CELLS AND PSYCHIATRIC DISORDERS

(71) Applicants: Dan R. Littman, New York, NY (US); Jun R. Huh, Newton, MA (US)

(72) Inventors: Dan R. Littman, New York, NY (US); Jun R. Huh, Newton, MA (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/042,976

(22) Filed: Feb. 12, 2016

(65) Prior Publication Data

US 2016/0257743 A1   Sep. 8, 2016

Related U.S. Application Data

(60) Provisional application No. 62/287,074, filed on Jan. 26, 2016, provisional application No. 62/115,799, filed on Feb. 13, 2015.

(51) Int. Cl.
| | |
|---|---|
| *A61K 39/395* | (2006.01) |
| *A61K 38/00* | (2006.01) |
| *A61K 9/46* | (2006.01) |
| *C07K 16/24* | (2006.01) |
| *C07K 16/28* | (2006.01) |
| *G01N 33/68* | (2006.01) |
| *C12Q 1/6883* | (2018.01) |

(52) U.S. Cl.
CPC ........ *C07K 16/244* (2013.01); *C07K 16/2866* (2013.01); *C12Q 1/6883* (2013.01); *G01N 33/6869* (2013.01); *C07K 2317/76* (2013.01); *C12Q 2600/118* (2013.01); *C12Q 2600/158* (2013.01); *G01N 2800/30* (2013.01)

(58) Field of Classification Search
None
See application file for complete search history.

(56) References Cited

PUBLICATIONS

Akintunde et al., J. Neuroimmunology, 2015, 286:33-41.*

* cited by examiner

*Primary Examiner* — Olga N Chernyshev
(74) *Attorney, Agent, or Firm* — Klauber & Jackson LLC

(57) ABSTRACT

Methods are presented herein for reducing the risk of developing a psychiatric disorder (e.g., autism like disorder) in a fetus involving administering an inhibitor of T helper 17 (Th17) cell activity to the mother of the fetus, while the mother is pregnant with the fetus at risk. Also encompassed herein is a method for treating a fetus in utero to reduce the risk of abnormal cortical development that arises from Th17 cell-mediated activity.

7 Claims, 15 Drawing Sheets

Specification includes a Sequence Listing.

MATERNAL TH17 CELLS AND PSYCHIATRIC DISORDERS

CROSS REFERENCE TO RELATED APPLICATIONS

This application claims priority under 35 USC § 119(e) from U.S. Provisional Application Ser. Nos. 62/287,074, filed Jan. 26, 2016 and 62/115,799, filed Feb. 13, 2015, each of which applications is herein specifically incorporated by reference in its entirety.

GOVERNMENT SUPPORT

The research leading to the present invention was funded in part by National Institutes of Health grants R00DK091508. The United States government has certain rights in the invention.

FIELD OF THE INVENTION

The present invention relates generally to reducing the risk for developing a psychiatric disorder [e.g., autism spectrum disorder (ASD), schizophrenia, and/or depression] in a fetus. More particularly, the present invention relates to a method for reducing the risk of developing a psychiatric disorder (e.g., ASD, of which autism is a particular example) in a fetus involving administering an inhibitor of T helper 17 (Th17) cell activity to the mother of the fetus, while the mother is pregnant with the fetus at risk. The method further relates to a method for treating a fetus in utero to reduce the risk of abnormal cortical development that arises from Th17 cell-mediated activity. Accordingly, the invention relates to the use and application of compounds or agents that inhibit Th17 activity for reducing fetal risk for developing a psychiatric disorder. In a further aspect, the invention relates to compounds or agents that inhibit Th17 activity for reducing fetal risk for developing a psychiatric disorder, such as ASD, and use of such compounds or agents in the preparation of a medicament for reducing fetal risk for developing a psychiatric disorder.

BACKGROUND OF THE INVENTION

Human studies suggest that maternal viral infection during pregnancy correlates with an increased frequency of Autism Spectrum Disorder (ASD) in the offspring (1-6). This observation has been modeled in rodents subjected to maternal immune activation (MIA) (7). The immune cell populations involved in induction of ASD-like behavior in the MIA model have not, however, been identified. A number of inflammatory cytokines and chemokines have been implicated in MIA, including tumor necrosis factor-α (TNF-α), IL-1β, and IL-8. Accordingly, information available to date demonstrates that a variety of inflammatory molecules contribute to MIA and thus, MIA is viewed as a generalized state of inflammation. See, for example, Harvey et al. (2014, Brain Behav Immun 40:27), Washington et al. (2015, Epilepsy Behav 50:40), and Ballendine et al. (2015, Prog Neuropsychopharmacol Biol Psychiatry 57:155), the entire content of each of which is incorporated herein by reference. The mechanism/s whereby inflammatory cytokines and chemokines contribute to MIA and MIA contributes to the development of autism and the specific immune cell population(s) involved are unknown.

The citation of references herein shall not be construed as an admission that such is prior art to the present invention.

SUMMARY OF THE INVENTION

As described herein, the present inventors utilize both genetic mutants and blocking antibodies to demonstrate that RORγt-dependent effector T lymphocytes [e.g. T helper 17 (Th17) cells] and the effector cytokine interleukin-17a (IL-17a) are required in mothers for MIA-induced behavioral abnormalities in their offspring. The present inventors also find that MIA induces an abnormal cortical phenotype, which is also dependent on maternal IL-17a, in the fetal brain. Results presented herein reveal that therapeutic targeting of Th17 cells and/or Th17 cell activity in susceptible pregnant mothers reduces the likelihood of bearing offspring/children with inflammation-induced ASD-like phenotypes.

In accordance with results presented herein, a method for reducing the risk of developing a psychiatric disorder in a fetus is presented, the method comprising administering an inhibitor of T helper 17 (Th17) cell activity to a pregnant female, wherein the pregnant female is carrying the fetus in utero.

In another aspect, a method for treating a fetus in utero to reduce risk of abnormal cortical development in the fetus is presented, the method comprising administering an inhibitor of T helper 17 (Th17) cell activity to a pregnant female carrying the fetus in utero.

In yet another aspect, a method for treating a pregnant female with elevated IL-17a levels is presented, the method comprising administering an inhibitor of Th17 cell activity to the pregnant female while the pregnant female is carrying a fetus to reduce inflammation in the pregnant female, thereby decreasing risk of abnormal cortical development in the fetus. As described herein, elevated IL-17a levels may be determined by comparing the pregnant female's IL-17a levels to those of a suitable control.

In a further aspect, a method for treating a pregnant female with a hyper-inflammatory condition is presented, the method comprising administering an inhibitor of Th17 cell activity to the female while pregnant with a fetus to reduce inflammation in the pregnant female, thereby decreasing risk for developing a psychiatric disorder in the fetus.

In yet a further aspect, method for decreasing symptoms of a psychiatric disorder in offspring of a pregnant female is described, the method comprising administering an inhibitor of Th17 cell activity to the pregnant female when the offspring is a fetus in utero to reduce Th17 cell activity in the pregnant female, thereby reducing risk of abnormal cortical development in the fetus associated with the psychiatric disorder and decreasing symptoms of the psychiatric disorder in the offspring.

The aforementioned methods may further comprise additional steps such as those set forth herein below.

In a particular embodiment of methods described herein, the psychiatric disorder observed in the offspring that developed from the fetus is autism spectrum disorder, schizophrenia, or depression. In a more particular embodiment thereof, the autism spectrum disorder is autism. In another particular embodiment, the psychiatric disorder is associated with fetal exposure to maternal inflammation.

In an aspect of methods described herein, the inhibitor of Th17 cell activity is administered to the female in the first, second, or third trimester of the pregnancy.

In another aspect of methods described herein, the methods may further comprise assaying IL-17a levels in a sample isolated from the pregnant female. Exemplary samples that may be isolated from the pregnant female and analyzed include, without limitation, whole blood, sera, amniotic fluid, and/or cerebrospinal fluid.

In a particular embodiment of methods described herein, the pregnant female has given birth to at least one offspring afflicted with a psychiatric disorder (such as, for example, ASD) in a previous pregnancy. In a further embodiment thereof, the previous pregnancy was the pregnant female's penultimate pregnancy (i.e., the most temporally recent) relative to the current pregnancy. Evaluation of IL-17a levels, for example, in pregnant females with a history of having given birth to offspring afflicted with a psychiatric disorder, particularly if the afflicted offspring was produced in the most recent birth, is recommended in light of the present findings and knowledge that siblings of afflicted offspring have a higher incidence of psychiatric disorders relative to those in unaffected families. In accordance with the present results, elevated IL-17a levels in the pregnant female that remain following a previous pregnancy may contribute to an increased risk of abnormal cortical development in a fetus exposed to elevated IL-17a levels in the current pregnancy and subsequent onset of a psychiatric disorder in offspring developing therefrom.

In yet another aspect of methods described herein, the pregnant female was or is afflicted with a hyper-inflammatory condition during the pregnancy with the fetus. In a particular embodiment thereof, the hyper-inflammatory condition is associated with a viral or bacterial infection or exposure to an inflammatory or environmental toxin during the pregnancy with the fetus. In further embodiments, the pregnant female was or is afflicted with the hyper-inflammatory condition during the first, second, or third trimester of the pregnancy with the fetus.

In a further aspect of methods described herein, the inhibitor of Th17 cell activity is administered to the pregnant female during or after the hyper-inflammatory condition. It may, for example, be administered to the pregnant female during the first, second, or third trimester of the pregnancy with the fetus.

As described herein, the inhibitor of Th17 cell activity may be an inhibitor of retinoic acid receptor-related orphan nuclear receptor gamma t (RORγt) activity and/or interleukin 17 (IL-17) activity or an enhancer of T regulatory (Treg) cell activity.

Exemplary inhibitors of RORγt activity include, without limitation, TMP778, SR1001, and SR2211.

Exemplary inhibitors of IL-17 activity include, without limitation, an antibody specific for a Th17 cell specific cytokine (such as, for example, IL-17f or IL-22) or a Th17 specific cell surface protein (such as, for example, CCR6, the IL-23 receptor, or the IL-17 receptor).

In a particular embodiment of methods described herein, the inhibitor of IL-17 activity is an antibody specific for IL-17a or the IL-17 receptor. In a more particular embodiment, the inhibitor of IL-17 activity is a human monoclonal antibody or a humanized monoclonal antibody. The human monoclonal antibody brodalumab (AMG 827) is, for example, envisioned for use in the present methods. The humanized monoclonal antibodies ixekizumab (LY2439821) and secukinumab (AIN457) are, for example, also envisioned for use in the present methods.

In another particular embodiment of methods described herein, the inhibitor of IL-17 activity is an antibody specific for the p19 subunit of IL-23, the p40 subunit of IL-23 and IL-12, or the IL-23 receptor. In a more particular embodiment thereof, the antibody specific for the p19 subunit of IL-23 is MK-3222 (SCH 900222), CNTO 1959, or AMG 139. In another particular embodiment thereof, the antibody specific for the p40 subunit of IL-23 and IL-12 is Stelara (ustekinumab; CNTO 1275).

In an aspect of methods described herein, the inhibitor of Th17 cell activity is administered orally or via intravenous, intrarterial, subcutaneous, intramuscular, intraperitoneal, or intrauterine injection.

In a particular embodiment of methods described herein, the inhibitor of Th17 cell activity is engineered such that it does not transfer across the placenta or is modified to reduce or prevent transfer across the placenta.

In a further aspect of methods described herein, the pregnant female does not have a pre-existing condition associated with aberrant Th17 cell activity. Such conditions may include multiple sclerosis, psoriasis, rheumatoid arthritis, or Crohn's Disease.

Other objects and advantages will become apparent to those skilled in the art from a review of the following description which proceeds with reference to the following illustrative drawings.

BRIEF DESCRIPTION OF THE DRAWINGS

(FIG. 1A) Serum concentrations of IL-6 (n=3-5 mice per group, 2 independent experiments) at 3 or 24 h after PBS or poly(I:C) injection into pregnant dams. (FIG. 1B) Serum concentrations of maternal IL-17a (n=4-8 mice per group, 2 independent experiments) at E14.5 in PBS- or poly(I:C)-injected mothers, pretreated with or without IL-17a blocking antibodies. (FIG. 1C and FIG. 1D) Relative IL-6 (FIG. 1C) and IL-17a (FIG. 1D) mRNA expression in cells isolated, and in vitro cultured for 24 h, from placenta/decidua of PBS- or poly(I:C)-treated mothers at E14.5. The results represent mean and standard error in two biological samples. For each probe set, relative mRNA expression of one biological replicate from PBS-treated dams was set at 1. Real-time PCR analysis of relative expression of indicated genes compared to the level of Gapdh in cells from PBS-treated dams. (FIG. 1E) Supernatant concentrations of IL-17a from ex vivo cultured mononuclear cells, isolated from placenta/decidua of PBS- or poly(I:C)-treated pregnant dams. Stim refers to PMA and Ionomycin stimulation. (FIG. 1F and FIG. 1G) Relative IL-17Ra (FIG. 1F) and IL-17Rc (FIG. 1G) mRNA levels in E14.5 male fetal brain, derived from PBS- or Poly(I:C)-injected mothers, pretreated with isotype control (Cont) or IL-17a blocking antibodies (anti-IL-17a). The relative mRNA fold change, compared to the PBS and Cont-treated group, is plotted on the y-axis (n=7 (PBS, Cont), n=7 (PBS, anti-IL-17a), n=7 (Poly(I:C), Cont), n=7 (Poly(I:C), anti-IL-17a); from 2-3 independent experiments). (FIG. 1H) In situ hybridization with an IL-17Ra RNA probe in E14.5 male fetal brains derived from PBS- or poly(I:C)-injected mothers. Images are representative of four independent experiments. (FIG. 1I) Relative signal intensity for images shown in (FIG. 1H). Scale bar represents 100 μm. (FIGS. 1A, B, E, F and G) One-way ANOVA with Tukey post-hoc tests. (FIGS. 1C, D and I) Student's t test. **$p<0.01$. Graphs show mean+/−s.e.m.

(FIG. 2A) Immuno-fluorescence staining of SATB2 (a marker of postmitotic neurons in superficial cortical layers) in E14.5 male fetal brain, derived from PBS- or poly(I:C)-injected mothers, pretreated with isotype control (Cont) or IL-17a blocking antibodies (anti-IL-17a). Images are representative of three independent experiments. Scale bar represents 100 µm. (MZ: marginal zone, CP: cortical plate, SP: subplate, SVZ: subventricular zone, VZ: ventricular zone). (FIG. 2C) Quantification of SATB2 intensity in the cortical region shown in (FIG. 2A) (n=8 (PBS, Cont), n=8 (PBS, anti-IL-17a), n=8 (Poly(I:C), Cont), n=8 (Poly(I:C), anti-IL-17a), 3 independent experiments). (FIG. 2B) Staining of SATB2 and TBR1 (a marker restricted to deeper cortical layers) in E18.5 male fetal brains from animals treated as in (FIG. 2A). II-IV, V and VI refer to different cortical layers. Images are representative of five independent experiments. Scale bar represents 100 µm. (FIG. 2D) Quantification of TBR1 and SATB2 positive cells in a 300×300 µm² region of interest (ROI) centered on the malformation in the cortical plate of E18.5 fetal brains (n=20 (PBS, Cont), n=20 (PBS, anti-IL-17a), n=24 (Poly(I:C), Cont), n=20 (Poly(I:C), anti-IL-17a), 5 independent experiments). (FIG. 2E) The spatial location of the cortical patch in E18.5 male fetal brains from poly(I:C)-injected mothers pretreated with control antibodies (n=20 (Poly(I:C),Cont)). (FIG. 2F) Ultrasonic vocalization (USV) assay. At P9, pups from the indicated experimental groups were separated from their mothers to elicit USV calls. The number of pup calls is plotted on the y-axis (n=25 (PBS, Cont), n=28 (PBS, anti-IL-17a), n=38 (Poly(I:C), Cont), n=34 (Poly(I:C), anti-IL-17a); from 6-7 independent experiments. (FIG. 2G) Social approach behavior. Graphed as a social preference index (% time spent investigating social or inanimate stimulus out of total object investigation time) (n=15 (PBS, Cont), n=15 (PBS, anti-IL-17a), n=16 (Poly(I:C), Cont), n=20 (Poly(I:C), anti-IL-17a); from 6-7 independent experiments. (FIG. 2H) Marble burying behavior. Percentage of the number of buried marbles is plotted on the y-axis (n=15 (PBS, Cont), n=15 (PBS, anti-IL-17a), n=15 (Poly(I:C), Cont), n=20 (Poly(I:C), anti-IL-17a); from 6-7 independent experiments. (FIG. 2I) Total distance traveled during social approach behavior. (FIGS. 2C, F, H and I) One-way ANOVA with Tukey post-hoc tests. (FIGS. 2D and G) Two-way ANOVA with Tukey post-hoc tests. **p<0.01 and *p<0.05. Graphs show mean+/−s.e.m.

(FIG. 3A) SATB2 and TBR1 staining in the cortex of E18.5 fetal brains following MIA induction with poly(I:C) in mothers with the indicated genotypes. II-IV, V and VI refer to different cortical layers. Images are representative of three independent experiments. Scale bar represents 100 µm. (FIG. 3B) Quantification of TBR1 and SATB2 positive cells in a 300×300 µm² ROI centered on the malformation in the cortical plate of E18.5 fetal brains (n=6 (PBS, WT), n=6 (Poly(I:C), WT), n=6 (Poly(I:C), RORγt-TKO)). (FIG. 3C) Number of ultrasonic vocalizations (USV)s emitted by P9 pups. Pups from the indicated maternal genotypes and treatment groups were separated from dams to elicit USV calls. Total USVs emitted during test period (3 min) are plotted on the y-axis (n=16, 18 and 15 offspring from PBS-treated WT, RORγt HET and RORγt TKO mothers; n=15, 11 and 28 from poly(I:C)-treated WT, RORγt HET and RORγt TKO mothers); data from 4-7 independent dams. (FIG. 3D) Social approach behavior is graphed as a social preference index (% time spent investigating social or inanimate stimulus/total exploration time for both objects). (n=21, 15 and 15 adult offspring from PBS-treated WT, RORγt HET and RORγt TKO mothers; n=36, 15 and 21 from poly(I:C)-treated WT, RORγt HET and RORγt TKO mothers); data from 4-7 independent dams. (FIG. 3E) Marble burying behavior is graphed as the percentage of buried marbles. (n=14, 19 and 15 adult offspring from PBS-treated WT, RORγt HET and RORγt TKO mothers; n=32, 15 and 25 from poly(I:C)-treated WT, RORγt HET and RORγt TKO mice per group); data from 4-7 independent dams. (FIG. 3F) Offspring tested for social behavior and marble burying show comparable total distance moved, regardless of their maternal genotypes or treatments. RORγt HET and RORγt TKO refer to RORγ$^{Neo/+}$; CD4-Cre/+ and RORγt$^{FL}$/RORγ$^{Neo}$; CD4-Cre/+, respectively. (FIG. 3C) One-way ANOVA with Holm-Sidak post-hoc tests. (FIGS. 3B and D) Two-way ANOVA with Tukey post-hoc tests. (FIGS. 3E and F) One-way ANOVA with Tukey post-hoc tests. *p<0.001, p<0.01 and *p<0.05. Graphs show mean+/−s.e.m.

(FIG. 4A) Schematic diagram of the experimental method. Each embryo was injected intraventricularly at E14.5 with PBS or recombinant IL-17a protein mixed with Fastgreen dye. (FIG. 4B) SATB2 and TBR1 staining in the cortex of E18.5 male fetal brains treated as in (FIG. 4A). Images are representative of five independent experiments. (FIG. 4C) Ultrasonic vocalization (USV) assay. At P9, pups from the indicated conditions were separated from their mothers to elicit USV calls. The number of pup calls is plotted on the y-axis (n=15 (PBS), n=17 (IL-17a); from 5-6 independent dams per treatment). (FIG. 4D) Social approach behavior. Graphed as a social preference index (% time spent investigating social or inanimate stimulus out of total object investigation time) (n=12 (PBS), n=18 (IL-17a), from 5-6 independent experiments). (FIG. 4E) Marble burying behavior. Percentage of the number of buried marbles is plotted on the y-axis (n=12 (PBS), n=18 (IL-17a), from 5-6 independent experiments). (FIG. 4F) Total distance traveled during social approach test. (FIGS. 4C, E and F) Student's t tests. (FIG. 4D) One-way ANOVA with Tukey post-hoc test. **p<0.01. Graphs show mean+/−s.e.m.

(FIG. 5A, B, C) Maternal serum concentrations of TNF-α, IFN-β and IL-1β (n=3-6 mice per group, pooled from two independent experiments) at 3, 24, 48 or 96 h after PBS or poly(I:C) injection of pregnant dams. (FIG. 5D) Serum and placenta/decidua concentrations of IL-10 at E15.5 (n=5-10 mice per group). (FIG. 5E) Serum concentrations of maternal IL-17a (n=5-8 mice per group, pooled from two independent experiments) at E14.5 in WT or IL-6 KO mothers injected with PBS, recombinant IL-6 (mIL-6), or poly(I:C). (FIG. 5F) Supernatant concentrations of IL-17a from ex vivo cultured mononuclear cells, isolated from duodenum of PBS- or poly(I:C)-treated pregnant dams. Stim refers to PMA and Ionomycin stimulation. One-way ANOVA with Tukey post-hoc tests. *p<0.001, p<0.01, *p<0.05 and ns; not significant Graphs show mean+/−s.e.m.

(FIG. 6A) Pregnant mothers of the indicated genetic background (or subjects of antibody treatment) at E12.5 were injected with PBS or poly(I:C) to induce MIA. (FIG. 6B) At E12.5, pregnant mothers were pretreated with isotype or anti-IL-17a blocking antibodies. 8 hours after the pretreatment, the mothers were injected with PBS or poly(I:C) to induce MIA. For histological analyses of cortical phenotypes, fetuses were sacrificed at E14.5 and E18.5. At P7 or P9, pups were separated from the mothers to measure USV calls. At ~8 wks, male offspring were subjected to the social approach test, which included 15 min of habituation over two consecutive days. At ~9 wks, the male offspring were subjected to the marble burying test.

(FIG. 7A) SATB2 and TBR1 immunofluorescence staining in the cortex of E18.5 male fetal brain, derived from PBS- or poly(I:C)-injected mothers. The disorganized patch of cortex observed in fetuses from poly(I:C)-injected mothers were categorized into groups based on morphology: Protrusion, Intrusion or other. Images are representative of 5-7 independent experiments. Scale bar represents 100 μm. (FIG. 7B) Percentage of the cortical patches in each category (n=24 (Poly(I:C), Cont)). (FIG. 7C) Thickness of the cortical plate in E18.5 fetal brains, derived from PBS- or poly(I:C)-injected mothers, pretreated with isotype control or IL-17a blocking antibodies (n=20 (PBS, Cont), n=20 (PBS, anti-IL-17a), n=20 (Poly(I:C), Cont), n=20 (Poly(I:C), anti-IL-17a), 5 independent experiments). One-way ANOVA with Tukey post-hoc tests. Graphs show mean+/−s.e.m.

(FIG. 8A) Coronal sections of the brains from adult offspring (P60) derived from PBS- or poly(I:C)-injected mothers, pretreated with isotype control or IL-17a blocking antibodies. Immunofluorescence staining with TBR1 (a marker for cortical layers 2, 3, 5 and 6), SATB2 (a marker more intensely expressed in superficial cortical layers), and CTIP2 (a marker restricted to layers 4-6) antibodies. Arrowheads indicate abnormal staining patterns in the cortex. Scale bar represents 100 μm. (FIG. 8B) Quantification of TBR1-, SATB2-, and CTIP2-positive cells in a 300-μm wide ROI centered on the malformation in the cortex of the adult brain (TBR1+ cells: n=4 (PBS, Cont), n=4 (PBS, anti-IL-17a), n=4 (Poly(I:C), Cont), n=4 (Poly(I:C), anti-IL-17a); SATB2+ cells: n=10 (PBS, Cont), n=10 (PBS, anti-IL-17a), n=10 (Poly(I:C), Cont), n=10 (Poly(I:C), anti-IL-17a); CTIP2+ cells: n=4 (PBS, Cont), n=4 (PBS, anti-IL-17a), n=4 (Poly(I:C), Cont), n=4 (Poly(I:C), anti-IL-17a)). Two-way ANOVA with Tukey post-hoc tests. **p<0.01. Graphs show mean+/−s.e.m.

(FIGS. 9A and B) Both gender ratio (FIG. 9A) and size (FIG. 9B) of litters following PBS versus poly(I:C) and control versus anti-IL17a treatments were measured upon weaning (n=68 (PBS, Cont), n=49 (PBS, anti-IL-17a), n=56 (Poly(I:C), Cont), n=61 (Poly(I:C), anti-IL-17a); from 8-9 dams per treatment). (FIG. 9C) Weight of the offspring from pregnant dams treated as in (FIG. 9A) and (FIG. 9B). 13~15-week-old male mice were used for measuring weights (n=20 (PBS, Cont), n=17 (PBS, anti-IL-17a), n=18 (Poly(I:C), Cont), n=17 (Poly(I:C), anti-IL-17a). (FIGS. 9A, B and C) One-way ANOVA with Tukey post-hoc tests. Graphs show mean+/−s.e.m.

(FIG. 10A-C) Flow cytometry of CD4+ T cells stained intracellularly for IL-17a and IFN-γ. Mononuclear cells were collected from placenta/decidua of PBS- or poly(I:C)-treated pregnant mice at E15.5 and E16.5. RORγ KO refers to a germline deletion mutant removing both RORγ and RORγt (RoRγ$^{Neo/Neo}$). (FIG. 10D, E) Flow cytometry of CD4+ T cells stained intracellularly for IL-17a (Th17) and FoxP3 (Treg). Mononuclear cells were collected from placenta/decidua of PBS- or poly(I:C)-treated pregnant mice at E14.5. (FIG. 10A-D) The cells were stimulated for 4-5 h with PMA/Ionomycin and stained for surface markers and intracellular cytokines. Each symbol represents an individual mouse. (FIG. 10A-E) Th17 refers to CD4+TCR-β+IL-17a+IFN-γ+/−, Th1 to CD4+TCR-β+IL-17a−IFN-γ+ and Treg to CD4+TCR-β+FoxP3+ cells. (FIG. 10F) Serum concentrations of maternal IL-17a (n=4 mice per group) at E18.5 in PBS- or poly(I:C)-injected WT or RORγt TKO mothers. (FIGS. 10A and D) Student's t test. (FIG. 10F) One-way ANOVA with Tukey post-hoc tests.***p<0.001 and *p<0.05. Graphs show mean+/−s.e.m.

FIG. 11A-E. Characterization of the disorganized cortical patch from intra-ventricular administration of IL-17a. (FIG. 11A) SATB2 and TBR1 staining of E18.5 fetal brains from animals treated as in (FIG. 4A). Images are representative of five independent experiments. (FIG. 11B) Thickness of the cortical plate in E18.5 fetal brains. (FIGS. 11A and B) (i), (ii) and (iii) indicate subdivisions resulting from equally dividing the cortex perpendicularly through the cortical plate. Scale bar represents 100 μm. (FIG. 11C) Quantification of TBR1 and SATB2 positive cells in a 300-μm wide ROI corresponding to the region of the cortical plate containing the malformation in E18.5 male fetal brain (n=20 (PBS), n=20 (IL-17a)). (FIG. 11D) The spatial location of the disorganized cortical patch in E18.5 fetal brain (n=20 (IL-17a)). (FIG. 11E) Percentage of the cortical patches in each category (n=20 (IL-17a)). (FIG. 11B) Student's t test. (FIG. 11C) Two-way ANOVA with Tukey post-hoc tests. **p<0.01, *p<0.05, and ns; not significant. Graphs show mean+/−s.e.m.

(FIG. 12A) SATB2 and TBR1 staining of the cortex in E18.5 fetal brains. PBS, IL-6 or IL-17a were intraventricularly injected into the fetal brain of the indicated genotypes at E14.5. Images are representative of 2-3 independent experiments. (FIG. 12B) Quantification of TBR1 and SATB2 positive cells in a 300×300 μm² ROI centered on the malformation in the cortical plate (n=6 (PBS, WT dam), n=6 (IL-6, WT dam), n=6 (IL-17a, IL-17Ra KO dam); from 2-3 independent dams per treatment). (FIG. 12C) Ultrasonic vocalization (USV) assay. At P9, pups from the indicated conditions in (A) were separated from their mothers to elicit USV calls. The number of pup calls is plotted on the y-axis (n=10 (PBS, WT dam), n=14 (IL-6, WT dam), n=20 (IL-17a, IL-17Ra KO dam); from 2-3 independent dams per treatment). (FIG. 12D) SATB2 and TBR1 staining in the cortex of E18.5 fetal brain, derived from PBS- or IL-6-injected mothers, pretreated with isotype control (Cont) or IL-17a blocking antibodies (anti-IL-17a). (FIG. 12E) Quantification of TBR1 and SATB2 positive cells in a 300×300 μm² ROI centered on the cortical plate containing the cortical patch (n=6 (PBS, Cont), n=6 (IL-6, Cont), n=6 (IL-6, anti-IL-17a); from 2-3 independent dams per treatment). (FIG. 12F) USV assay for the pups from the indicated conditions as (FIG. 12D) (n=10 (PBS, Cont), n=19 (IL-6, Cont), n=18 (IL-6, anti-IL-17a); from 3-4 independent dams per treatment). (FIG. 12G) USV assay for the pups injected with PBS or IL-17a and derived from IL-6 KO mothers injected with Poly(I:C) (n=8 (PBS,Poly(I:C)), n=10 (IL-17a,Poly(I:C)); from 2 independent dams per treatment). (FIGS. 12B and E) Two-way ANOVA with Tukey post-hoc tests. (FIGS. 12C and F) One-way ANOVA with Tukey post-hoc tests. (FIG. 12G) Student's t test. **p<0.01, *p<0.05 and ns; not significant. Graphs show mean+/−s.e.m.

(FIG. 14A) Schematic diagram of the experimental design. At E12.5, pregnant mothers were injected with PBS or poly(I:C) to induce MIA. Two days later (E14.5), the pregnant mothers were treated with isotype or anti-IL-17a blocking antibodies. At P7~P9, pups were separated from the mothers to measure USV calls. At ~8 wks, male offspring were subjected to the social approach test and marble burying test. (FIG. 14B) Ultrasonic vocalization (USV) assay. At P9, pups from the indicated conditions were separated from their mothers to elicit USV calls. The number of pup calls is plotted on the y-axis (n=17 (PBS+Cont), n=17 (Poly(I:C)+Cont), n=27 (Poly(I:C)+anti-IL-17a; from 3-4 independent dams per treatment). (FIG. 14C) Social approach behavior. Graphed as a social preference index (% time spent investigating social or inanimate stimulus out of total object investigation time) (n=12 (PBS+Cont), n=10 (Poly(I:C)+Cont), n=17 (Poly(I:C)+anti-IL-17a; from 3-4 independent dams per treatment). (FIG. 14D) Marble burying behavior. Percentage of the number of buried marbles is plotted on the y-axis (n=12 (PBS+Cont), n=10 (Poly(I:C)+Cont), n=17 (Poly(I:C)+anti-IL-17a; from 3-4 independent dams per treatment). (FIG. 14E) Total distance traveled during social approach behavior. (FIGS. 14B, D and E) One-way ANOVA with Tukey post-hoc tests. (FIG. 14C) Two-way ANOVA with Tukey post-hoc test. $**p<0.01$ and $*p<0.05$. Graphs show mean+/−s.e.m.

(FIG. 15A) Schematic diagram of targeting strategy and affected allele. (FIG. 15B) Southern blot analysis with ES cell genomic DNA after homologous recombination. Southern blot with Probe A following EcoRV (RV) digestion produced an 8.9 kb band for WT and a 7.3 kb band for the targeted allele. Southern blot with Probe B following EcoRI (RI) digestion produced a 15.1 kb band for WT and a 6.5 kb band for the targeted allele. (FIG. 15C) Southern blot with Probe A following EcoRV and XhoI (XH) digestion confirmed Cre-dependent generation of the mutant allele (Conditional allele: 7.4 kb; mutant allele: 5.6 kb). DNA was prepared from the RORγt conditional ES cells, with or without Cre transfection.

DETAILED DESCRIPTION

Figure 1:
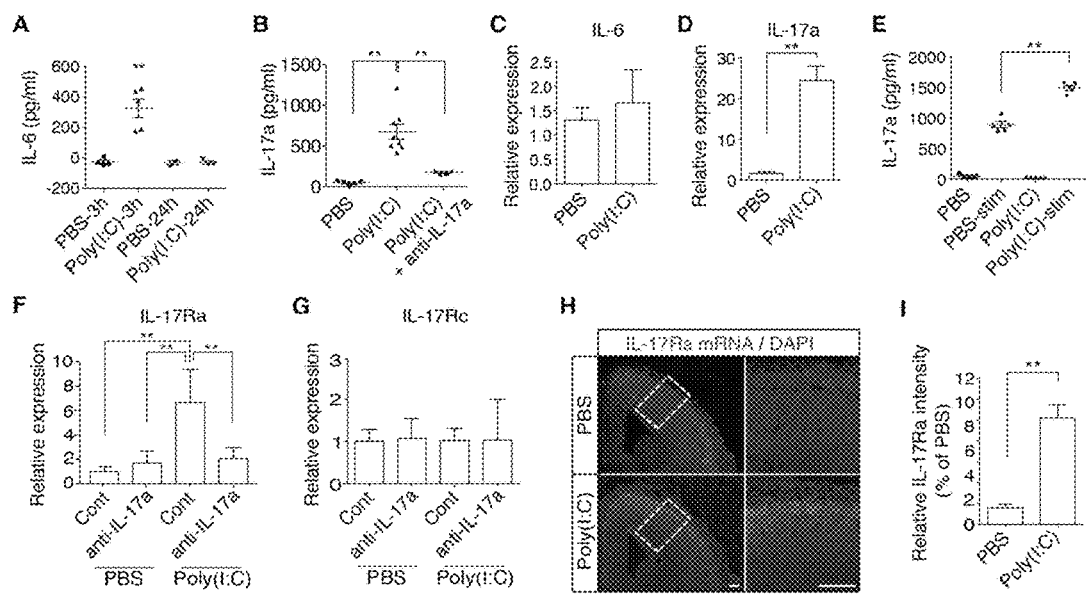
FIG. 1A-I. IL-17a increase in mothers subjected to MIA leads to elevated IL-17Ra mRNA expression in the offspring.

In the rodent model of MIA, offspring from pregnant mice exposed to viral infection or intra-peritoneal injection of synthetic dsRNA (poly(I:C)) mimicking viral infection exhibit behavioral symptoms reminiscent of ASD: social deficits, abnormal communication and repetitive behaviors (8). Th17 cells are responsible for immune responses against extracellular bacteria and fungi, and their dysregulation is thought to underlie numerous inflammatory and autoimmune diseases (9), such as asthma, rheumatoid arthritis, psoriasis, inflammatory bowel disease (IBD) and multiple sclerosis. The transcription factor, Retinoic acid receptor-related Orphan nuclear Receptor gamma t (RORγt) is expressed in several cell types in the immune system. It is a key transcriptional regulator for the development of Th17 cells as well as γδ T cells and innate lymphoid cells (such as ILC3) that express Th17 cell-like cytokines, in both humans and mice (10-13).

Several studies have suggested a role of Th17 cells and their cytokine mediators in ASD. For example, elevated levels of IL-17a, the predominant Th17 cytokine, have been detected in the serum of a subset of autistic children (14, 15). A genome-wide copy number variant (CNV) analysis identified il17a as one of many genes enriched in autistic patients (16). Similarly, in the MIA mouse model, $CD4^+$ T lymphocytes from affected offspring produced higher levels of IL-17a upon in vitro activation (17, 18). While these data suggest that the Th17 cell pathway is involved in ASD, whether Th17 cells are the specific immune cell population that is necessary for MIA phenotypes is not known. Further to this point, it is noteworthy that numerous other inflammatory cytokines have been implicated in MIA. See, for example, Harvey et al. (2014, Brain Behav Immun 40:27), Washington et al. (2015, Epilepsy Behav 50:40), and Ballendine et al. (2015, Prog Neuropsychopharmacol Biol Psychiatry 57:155), the entire content of each of which is incorporated herein by reference. These references underscore the complexity of the inflammatory response manifest in MI.

The present inventors chose to investigate the potential role of Th17 cell signaling in MIA so as to explore its contribution to behavioral abnormalities in offspring. As described herein, the present inventors show that maternal RORγt-expressing pro-inflammatory T cells, a major source of IL-17a, are required in the MIA model for induction of ASD-like phenotypes in offspring. Consistent with this notion, antibody blockade of IL-17a activity in pregnant mice protected against the development of MIA-induced behavioral abnormalities in the offspring. Importantly, the present inventors also found atypical cortical development in affected offspring, and this abnormality was rescued by inhibition of maternal Th17/IL-17a pathways.

Results presented herein show that pregnant mothers injected with poly(I:C) on embryonic day 12.5 (E12.5) had strong induction of serum IL-6, TNF-α, IFN-β and IL-1β levels at 3 h, compared with PBS-injected control dams (FIGS. 1A and 5A-C). Additionally, poly(I:C) injection resulted in a strong increase of serum IL-17a at E14.5 (FIG. 1B). On the other hand, poly(I:C) did not affect the levels of the anti-inflammatory cytokine IL-10 in the serum nor in placenta and decidua extracts (FIG. 5D). It was previously shown that the pro-inflammatory effector cytokine IL-6, a key factor for Th17 cell differentiation (19), is required in pregnant mothers for MIA to produce ASD-like phenotypes in the offspring (7). The present inventors found that poly (I:C) injection into pregnant dams lacking IL-6 (IL-6 KO) failed to increase the serum levels of IL-17a at E14.5, consistent with IL-6 acting upstream of IL-17a. Conversely, recombinant IL-6 injections into wild-type (WT) mothers were sufficient to induce IL-17a levels comparable to those of poly(I:C)-injected WT mothers (FIG. 5E). Placenta- and decidua-associated mononuclear cells, isolated from poly(I:C)-treated animals at E14.5 and cultured for 24 h, expressed similar levels of IL-6 mRNA compared to PBS controls (FIG. 1C). In contrast, IL-17a mRNA expression in these cells was strongly up-regulated by poly(I:C) injection (FIG. 1D). This increase in mRNA expression was correlated with enhanced secretion of IL-17a by placenta- and decidua-associated mononuclear cells from poly(I:C)-treated dams (FIG. 1E), upon ex vivo stimulation with phorbolmyristate acetate (PMA) and ionomycin that mimics T cell receptor (TCR) activation. IL-17a induction was specific to the placenta and decidua, as small intestine mononuclear cells from poly(I:C)-treated pregnant dams did not secrete higher levels of IL-17a than those from PBS-treated controls (FIG. 5F). The present inventors also observed that expression of the IL-17a receptor subunit A (IL-17Ra), but not subunit C (IL-17Rc), mRNA was strongly augmented in the fetal brain upon induction of MIA (FIGS. 1F and G). By in situ hybridization, IL-17Ra mRNA was detected in the mouse cortex, and its expression was strongly up-regulated in E14.5 fetal brains following poly(I:C) injection of pregnant dams (FIGS. 1H and I). The in situ probe detecting endogenous expression of IL-17Ra was, moreover, demonstrated to be specific.

Figure 2:
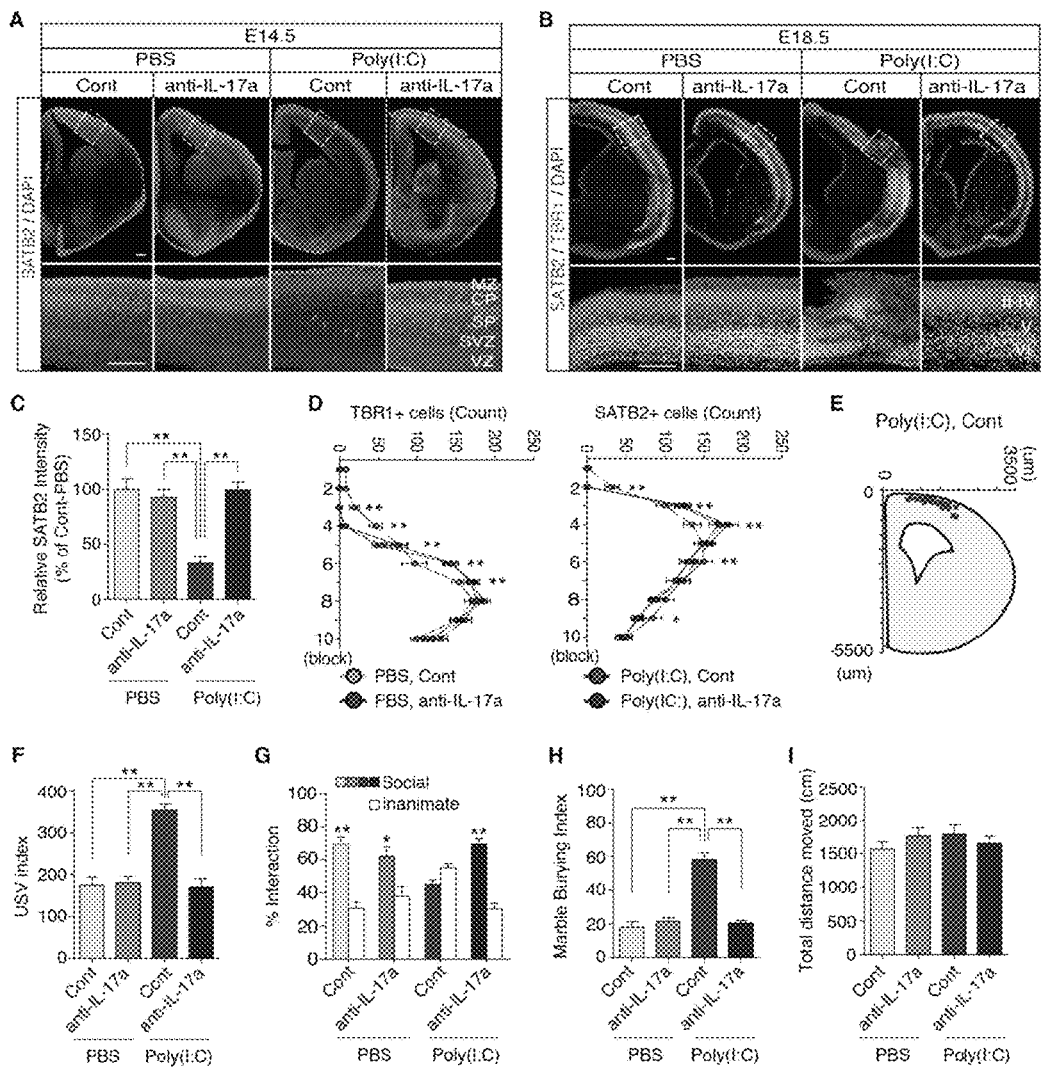
FIG. 2A-I. The IL-17a pathway promotes abnormal cortical development and ASD-like behavioral phenotypes in the offspring of pregnant dams following MIA.
Figure 6:
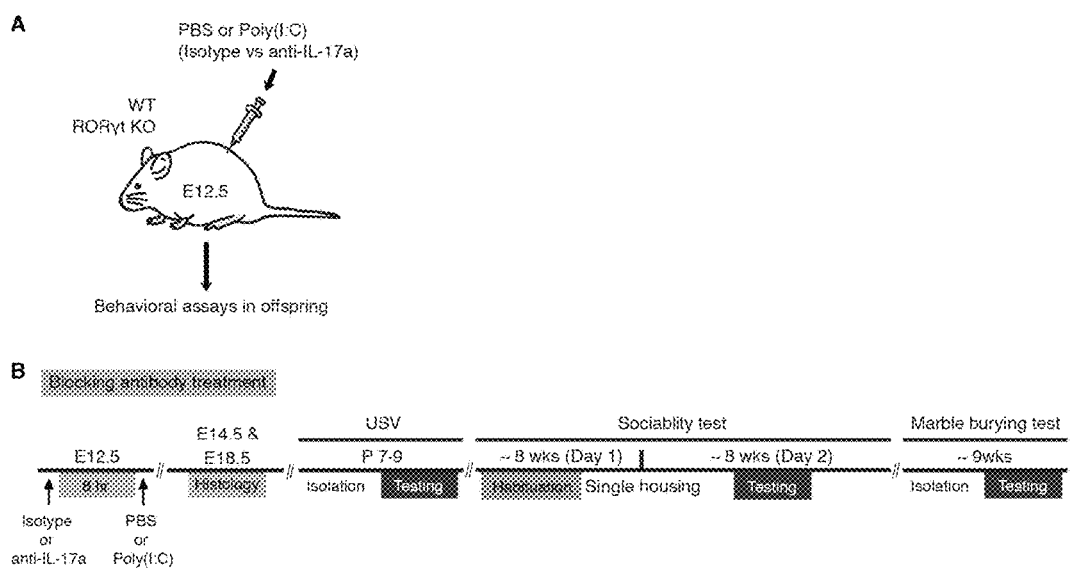
FIG. 6A-B. Schematic diagram of the experimental design.
Figure 7:
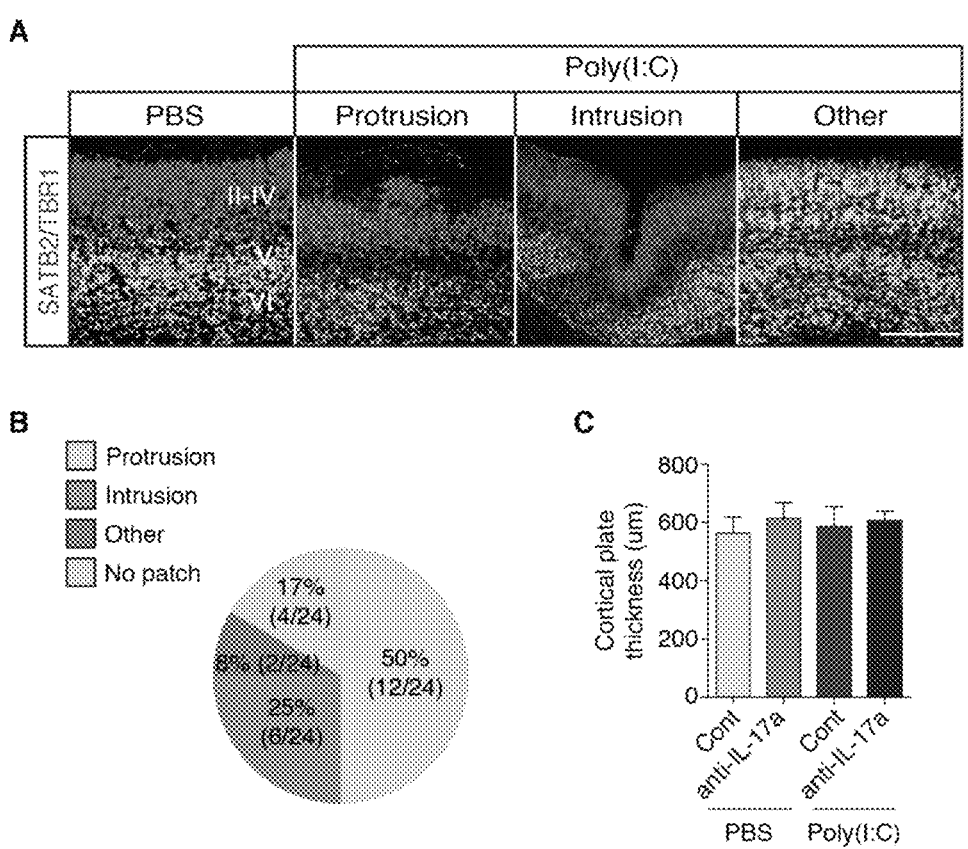
FIG. 7A-C. Categorization of the disorganized cortical patch in the fetal brain following MIA induction in the mother.
Figure 8:
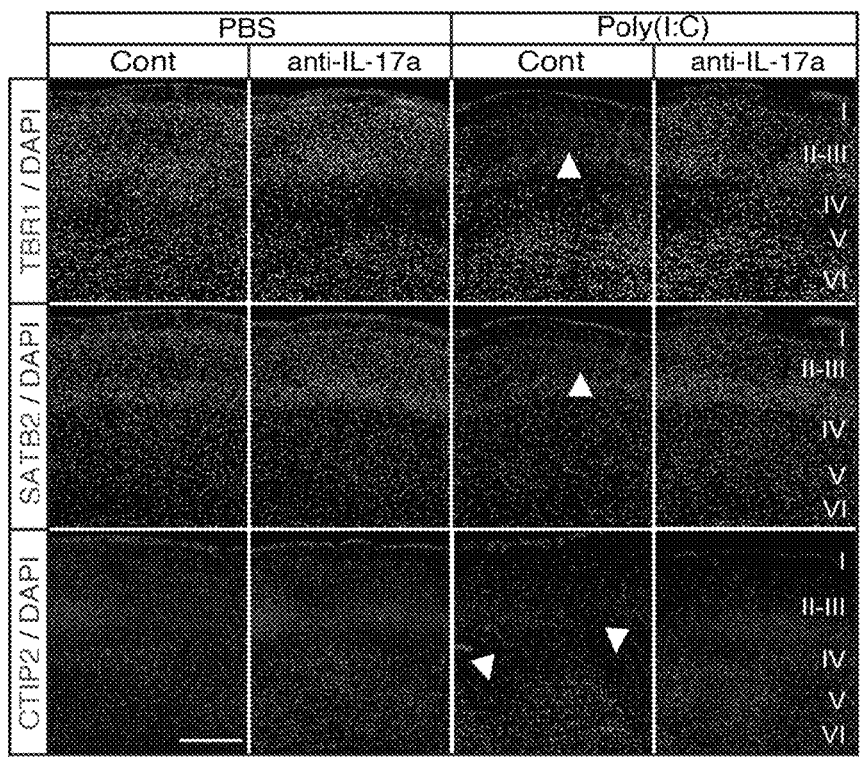
FIG. 8A-B. Abnormal cortical development in adult offspring of mothers subjected to MIA.
Figure 8:
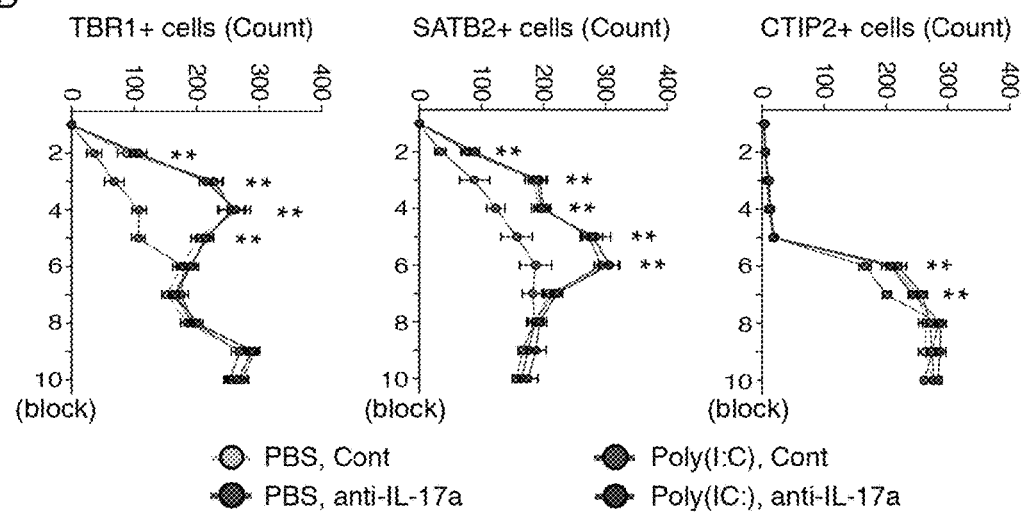

The present inventors next investigated if pathological activation of the IL-17 pathway in pregnant mothers affects fetal brain development and subsequently contributes to the ASD-like behavioral phenotypes in offspring. To test this hypothesis, pregnant mothers were pretreated with isotype control or IL-17a blocking antibodies before injecting them with PBS or poly(I:C) (FIG. 6). The present inventors then examined cortical development in the fetus for the following reasons: 1) Poly(I:C) injection of mothers increases IL-17Ra expression in the cortex of the fetal brain (FIGS. 1H and I); 2) Cortical development starts approximately at E11 (20), which aligns well with the time points of potential fetal exposure to MIA (7); 3) Disorganized cortex and focal patches of abnormal laminar cytoarchitecture have been found in the brains of ASD patients (21, 22); and 4) MIA has been shown to affect cortical development (23, 24). Cortical lamination was examined in fetal brains at E14.5 and E18.5 as well as in the adult brain using antibodies specific for proteins expressed in the cortex in a layer-specific manner (25): Special AT-rich sequence-binding protein 2 (SATB2) (26), T-brain-1 (TBR1) (27), and chicken ovalbumin upstream promoter transcription factor-interacting protein 2 (CTIP2) (28). MIA led to delayed expression of SATB2 at E14.5 compared with fetuses of control animals (FIG. 2A, C). At E18.5, MIA resulted in a patch of disorganized cortical cytoarchitecture (FIG. 2B, D-E and FIGS. 7A and B) but did not affect cortical thickness of the fetal brains (FIG. 7C). This singular patch of disorganized cortex occurred at a similar medial-lateral position in a majority of E18.5 fetal brains examined (FIGS. 2E and 7B). The abnormal expression patterns of SATB2, TBR1 and CTIP2 were maintained in adult MIA offspring (FIG. 8). Importantly, normal expression of these cortical layer-specific markers, as well as laminar cortical organization, were largely preserved in the offspring of poly(I:C)-injected mothers pretreated with IL-17a blocking antibody (FIGS. 2A-D and 8). Pretreatment with IL-17a blocking antibody also suppressed the MIA-mediated increase in IL-17Ra mRNA expression in fetal brain at E14.5 (FIG. 1F). This suppression was accompanied by a reduction in maternal serum IL-17a (FIG. 1B), indicating that the upregulation of IL-17Ra mRNA in fetal brains requires maternal IL-17a signaling. Of note, IL-17a antibody blockade of the IL-17a/IL-17Ra signaling pathway did not result in a concomitant increase of the serum IL-10 levels, and IL-17a mRNA expression was not detected in fetal brain at E14.5, regardless of poly(I:C) injection. Together, these data demonstrate that the maternal IL-17a-dependent pathway mediates disorganized cortical phenotypes in offspring following in utero MIA and suggest that this may be due to exposure of the fetus and its brain to increased levels of IL-17a.

Figure 9:
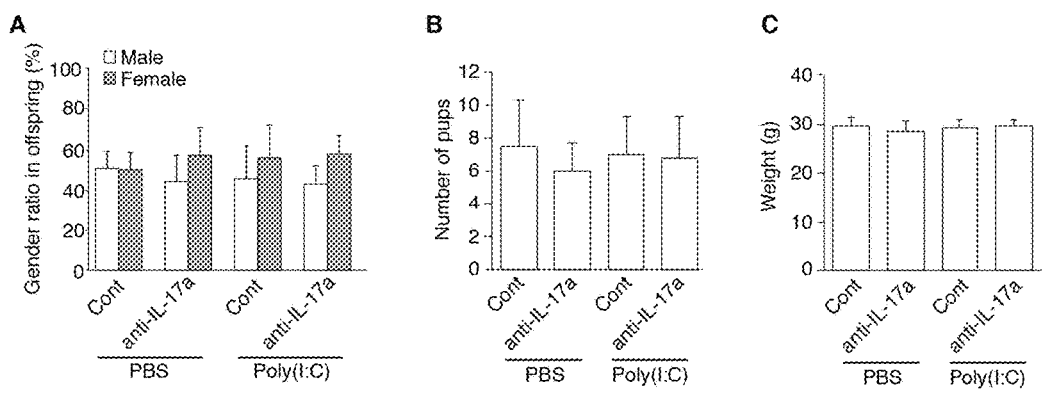
FIG. 9A-C. Properties of the litter are not affected by poly(I:C) or anti-IL-17a treatment.

The present inventors next tested the functional relevance of the maternal IL-17a pathway for MIA-induced ASD-like behavioral abnormalities in offspring (FIG. 6). MIA offspring were initially assessed for abnormal communication by measuring pup ultrasonic vocalization (USV) responses (29). Following separation from mothers, pups from poly(I:C)-injected mothers pretreated with IgG isotype control antibody emitted more USV calls than those from PBS-injected mothers (FIG. 2F), in agreement with previous studies (29, 30). Some studies have reported reduced USV calls upon MIA (8, 31), but these opposite effects may reflect differences in methodological approaches, including dose and number of exposures to poly(I:C) as well as timing of poly(I:C) administration. Altogether, these results indicate that MIA induces abnormal USV in offspring. Pretreating poly(I:C)-injected mothers with IL-17a blocking antibody resulted in offspring that emitted a similar number of USV calls as the pups from PBS-injected control mothers (FIG. 2F), demonstrating that IL-17a-mediated signaling events are necessary for the MIA-induced abnormal USV phenotype. As previously reported (7, 8), the present inventors found that prenatal exposure to MIA also caused social interaction deficits in adult offspring (FIG. 2G). This defect was fully rescued in offspring from poly(I:C)-injected mothers pretreated with IL-17a blocking antibody (FIG. 2G). Repetitive/perseverative behaviors are another core feature in ASD that were tested in the experimental mice described herein using the marble burying assay (32). Offspring from poly(I:C)-injected mothers displayed enhanced marble burying compared with offspring from PBS-injected mothers (FIG. 2H), consistent with previous studies (7, 29). Pretreatment with IL-17a blocking antibody of poly(I:C)-injected mothers rescued marble burying behavior in the offspring (FIG. 2H). Importantly, distinct behavioral phenotypes observed among different treatment groups were not due to differences in activity or arousal as total distances moved during the sociability or marble burying tests were indistinguishable (FIG. 2I). Moreover, different treatment groups displayed comparable gender ratios, litter sizes, and weights (FIG. 9). Taken together, these data indicate that the IL-17a pathway in pregnant mice is crucial in mediating the MIA-induced behavioral phenotypes in offspring.

Figure 3:
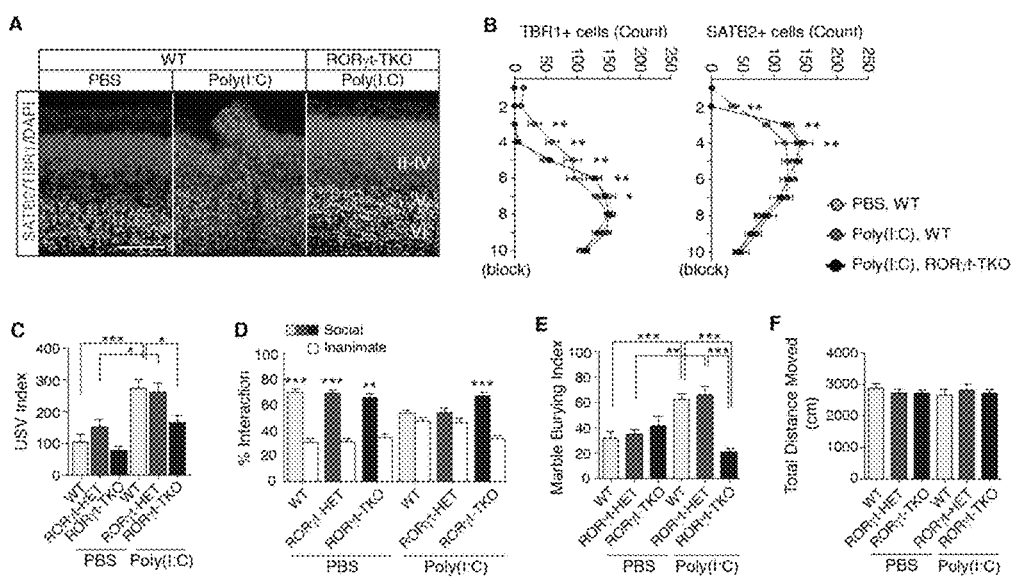
FIG. 3A-F. RORγt expression in maternal T cells is required for manifestation of ASD-like phenotypes in the MIA model.
Figure 10:
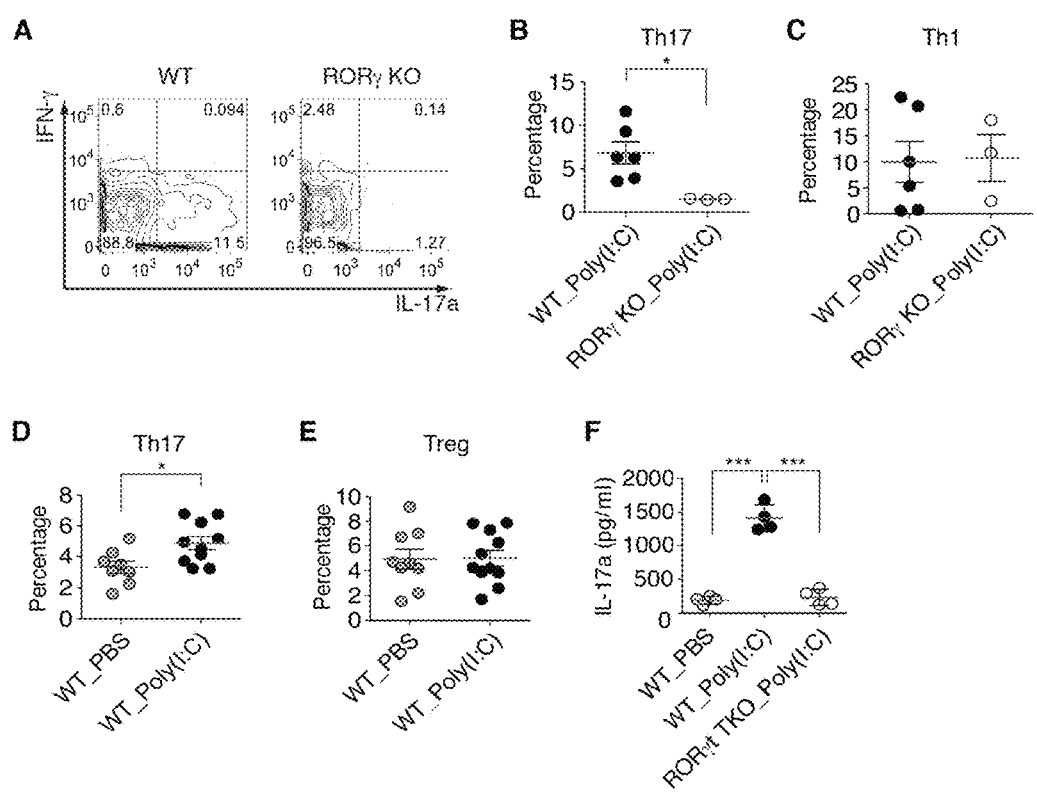
FIG. 10A-F. Th17 cells in the placenta and decidua of pregnant mice experiencing MIA.

As RORγt is a critical regulator of the IL-17a pathway (13), the present inventors next investigated the role of maternal RORγt in MIA-induced behavioral phenotypes in offspring. Importantly, Th17 cells and IL-17a have been detected in the decidua as well as in the serum during pregnancy in humans (33-35). CD45$^+$ mononuclear cells, including CD4$^+$ T cells, isolated from placenta and decidua of immune-activated WT mothers, but not from immune-activated mothers lacking both RORγt and the closely related RORγ isoform (RORγ KO), produced IL-17a upon ex vivo activation with PMA and ionomycin (FIGS. 10A and B). Cells isolated from WT and RORγ KO mice secreted similar amounts of IFN-γ, consistent with the specific effect of RORγt on IL-17a expression (FIG. 10C). In line with this observation, poly(I:C) treatment increased placenta/decidua-associated Th17 but not regulatory T (Treg) cells in pregnant dams, compared with PBS treatment (FIGS. 10D and E). RORγ KO mice lack RORγ/γt expression not only in CD4$^+$ T cells, but also in other lymphoid and non-immune system cells, and they have defective development of secondary and tertiary lymphoid organs (36, 37). To determine if RORγt function in T cells specifically mediates MIA-induced phenotypes, RORγt$^{FL}$ animals were bred to CD4-Cre mice to selectively inactivate rorc(t) in the T cells of pregnant mothers (RORγt TKO) (38). In these animals, the functions of Th17 cells (CD4$^+$RORγt$^+$ cells) and other RORγt-expressing αβT cells are inhibited, but there is no effect in RORγt-expressing innate (or innate-like) immune cells, including γδT, lymphoid tissue-inducer (LTi) cells, and innate lymphoid cells type 3 (ILC3) (11, 12), as well as in RORγ-expressing non-lymphoid cells. The present inventors found that RORγt TKO mothers failed to produce IL-17a even after poly(I:C) injection (FIG. 10F). Importantly, poly(I:C)-induced malformation of the cortex was prevented in offspring from RORγt TKO mothers (FIGS. 3A and B), similar to anti-IL-17a treatment (FIGS. 2B and D). Moreover, the present inventors found that prenatal exposure to MIA increased USV calls in pups derived from WT or RORγt HET mothers, but offspring of RORγt TKO mothers had normal USV behavior (FIG. 3C). T cell-specific deletion of maternal RORγt also abrogated the MIA-induced social interaction deficit and excessive marble burying in offspring (FIGS. 3D and E). These results were not due to general activity defects in the offspring of WT, RORγt HET, or TKO mothers (FIG. 3F). Since these offspring were derived from mating RORγt WT/HET/TKO female with WT male mice, they all carried at least one copy of functional RORγt. Therefore, the rescue of MIA-induced phenotypes observed in the offspring of RORγt TKO mothers was not likely due to the lack of Th17 cells in the offspring. Taken together, these data indicate that maternal CD4+ T lymphocytes expressing RORγt (i.e. Th17 cells) are necessary for the MIA-mediated expression of cortical abnormalities and three ASD-like behaviors modeled in mouse offspring.

The above results do not, however, preclude the possibility that related T cells, such as, for example, CD8 and γδTCR T cells with a similar RORγt-dependent cytokine program may also contribute to MIA and resultant cortical abnormalities and ASD-like behaviors in offspring.

Figure 11:
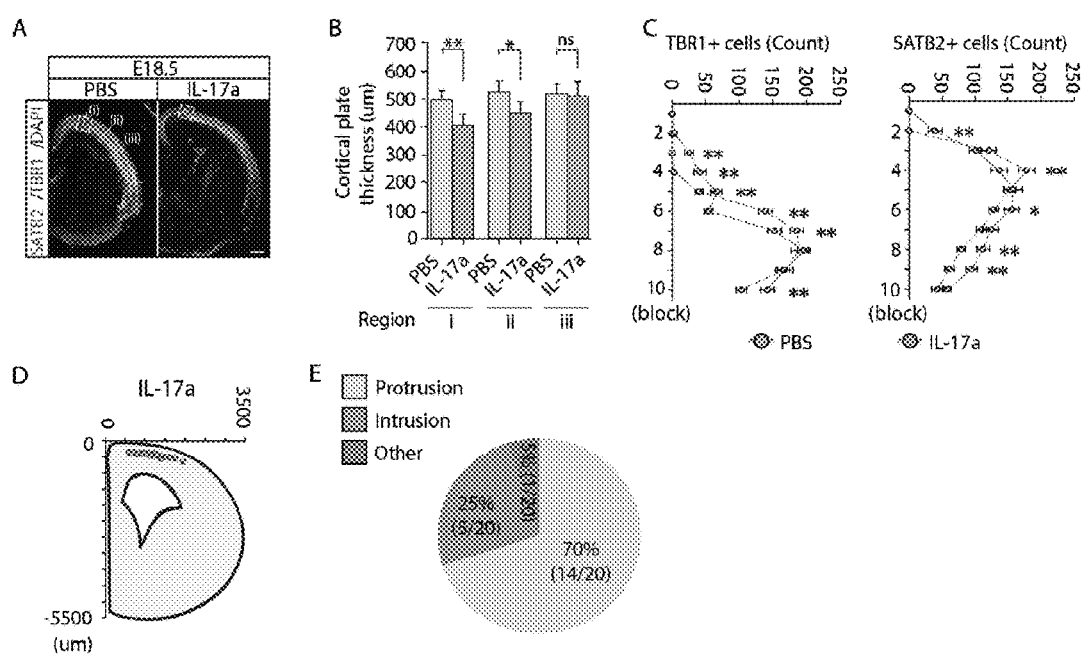

To test the functional significance of the IL-17Ra in offsring with a full germline il17ra KO without affecting maternal Th17 cell activity, the present inventors asked if increasing IL-17Ra activity in the offspring by introducing IL-17a directly into the fetal brain in the absence of maternal inflammation would be sufficient to induce MIA phenotypes. Injection of recombinant IL-17a protein into the ventricles of the fetal brain at E14.5 in the absence of MIA (FIG. 4A and FIG. 11) led to the appearance of disorganized cortical patches in a similar location to those induced by MIA (FIG. 4B, 11C-E). Unlike poly(I:C) injection, however, intraventricular injection of IL-17a resulted in thinned cortical plates at the medial but not lateral part of the brain (FIG. 11B). This effect may reflect differences in the levels or types of inflammation associated with poly(I:C) versus IL-17a injections or the time points at which poly(I:C) (E12.5) and IL-17a (E14.5) were administered. The present inventors also found that, compared with sham injection, IL-17a injections led to an enhanced USV phenotype, social approach deficit and increased marble burying behavior, all similar in magnitude to that observed in MIA-exposed offspring (FIG. 4C-E). These behavioral abnormalities were not due to group differences in mobility (FIG. 4F). Importantly, neither cortical disorganization nor enhanced USV phenotypes were observed following IL-17a injections into the ventricles of IL-17Ra KO fetuses or upon IL-6 injections into WT fetal brains (FIG. 12A-C), suggesting that IL-17a, but not IL-6, acts directly in the fetal brain to induce these phenotypes. Of note, in agreement with previous reports (7, 40), IL-6 injection into pregnant WT mothers was sufficient to produce MIA-associated behavioral (enhanced USV) and cortical phenotypes in the offspring (FIG. 12D-F). Importantly, pretreatment of pregnant mothers with anti-IL-17a blocking antibody prevented the phenotypes induced by maternal IL-6 injection (FIG. 12D-F). Lastly, IL-17a injection into brains of fetuses from poly(I:C)-injected IL-6 KO mothers was sufficient to elicit increased pup USVs compared with PBS-injected controls (FIG. 12G). These data collectively demonstrate that activation of the IL-17Ra pathway in the fetal brain, induced by intra-ventricular injection of IL-17a into the fetus or by intra-peritoneal injection of poly(I:C) or IL-6 into pregnant mothers, results in MIA-associated phenotypes in the offspring.

Figure 13:
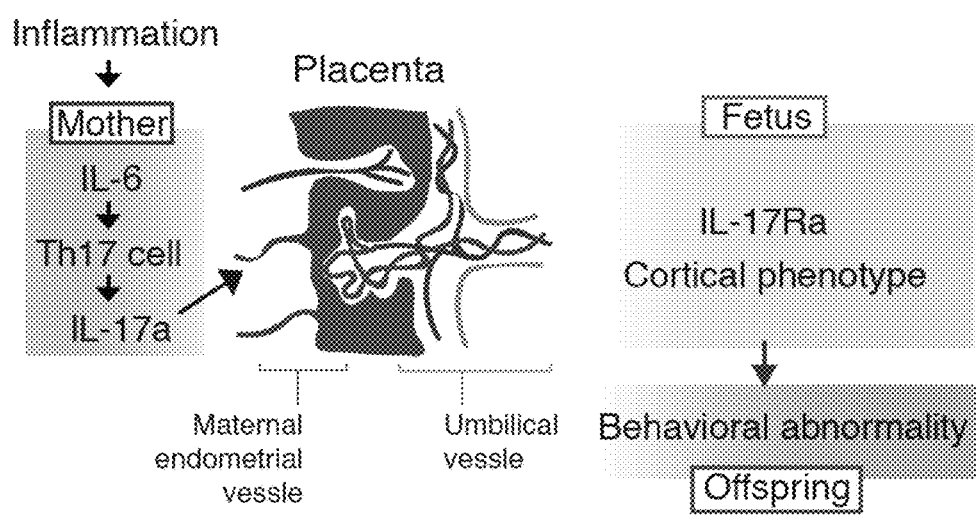
FIG. 13. A proposed mechanism by which maternal Th17 cells and IL-17a induce MIA-dependent behavioral and cortical abnormalities in offspring.
Figure 14:
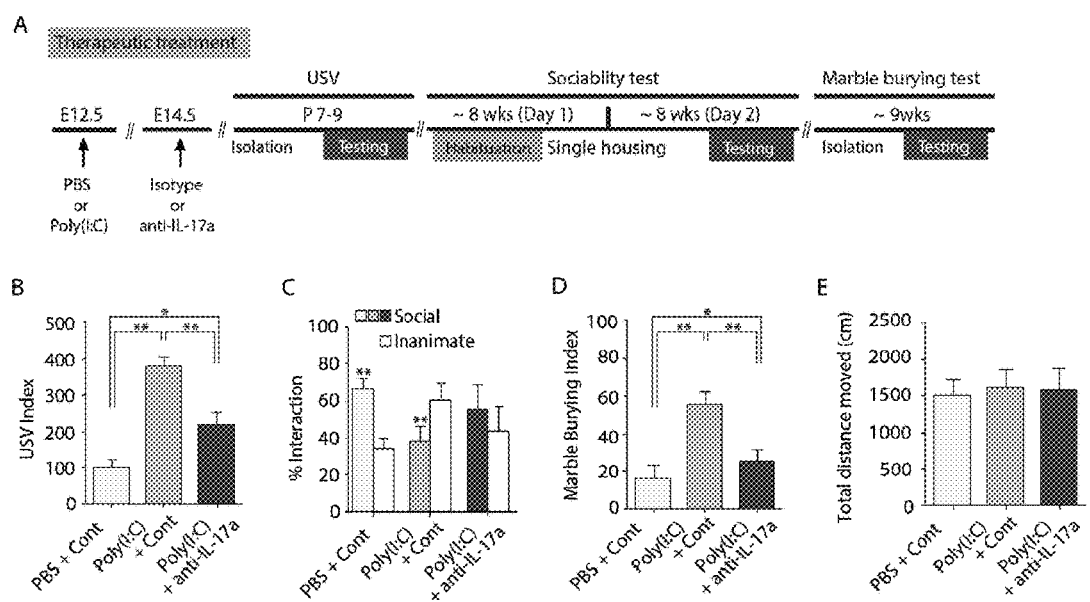
FIG. 14A-E. Therapeutic effects of blocking IL-17a signaling in pregnant dams.

Results presented herein suggest that pathological activation of the Th17 cell/IL-17 pathway during gestation in mothers with some inflammatory conditions may alter fetal brain development and contribute to the ASD-like behavioral phenotypes in offspring (FIG. 13). Th17 cells require RORγt for their differentiation and exert their functions by secreting multiple cytokines, including IL-17a. Abrogation of RORγt expression in maternal αβ T cells or blockade of the IL-17 pathway in pregnant dams resulted in the complete rescue of cortical developmental abnormalities and ASD-like behavioral phenotypes in offspring in the MIA rodent model. Thus, RORγt and Th17 cells (as well as their cytokines) may serve as good therapeutic targets to prevent the development of ASD phenotypes in the children of susceptible mothers. To further test this idea, the present inventors administered anti-IL-17a antibody to pregnant mice in a time window following MIA induction (FIG. 14A). Pregnant mothers were injected with PBS or poly(I:C) at E12.5, followed by injection of IgG isotype control or anti-IL-17a blocking antibody at E14.5, when the delayed expression of SABT2 manifests in MIA-exposed fetal brains (FIGS. 2A and C). Compared to PBS injection followed by control antibody treatment, poly(I:C) injection followed by anti-IL-17a antibody administration partially rescued USV and marble burying phenotypes (FIGS. 14B and D). However, MIA-induced social interaction deficits were not corrected (FIG. 14C). These effects were not due to group differences in mobility (FIG. 14E). Thus, treating pregnant mothers with anti-IL-17a after MIA can correct some of the ASD-like features, but pretreatment with anti-IL-17a antibody has greater therapeutic potential.

Based on their understanding of the field, the present inventors believe that this is the first identification of a specific immune cell population that may have direct roles in inducing ASD-like phenotypes. See also Choi et al. (2016, Science pii: aad0314 [Epub ahead of print], the entire content of which is incorporated herein by reference.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

In a broad aspect, methods are disclosed herein for reducing a fetus' risk of developing a psychiatric disorder [e.g., autism spectrum disorder (ASD), schizophrenia, and/or depression], wherein such methods call for administering inhibitors of Th17 cell activity to the female carrying the fetus in utero (i.e., the fetus' mother) during the pregnancy. Such methods encompass reducing the risk of developing autism in a fetus in mammals and, more particularly, in humans, using agents or compounds that inhibit Th17 activity. In a particular aspect, methods are provided for reducing the risk of developing a psychiatric disorder in a fetus, comprising administration of one or more agents or compounds that inhibit Th17 cell activity to the fetus' mother while the mother is pregnant with the fetus. The method further relates to a method for treating a fetus in utero to reduce the risk of abnormal cortical development that arises from Th17 cell-mediated activity and thus, reduces the fetus' risk of developing a psychiatric disorder after birth. The use of one or more agents or compounds that inhibit Th17 cell activity for reducing the risk of developing a psychiatric disorder in a fetus is also encompassed herein as is its/their use in the preparation of a medicament for reducing risk of developing a psychiatric disorder in a fetus. Such agents and compounds inhibit Th17 cell activity in the pregnant mother carrying the at risk fetus and in so doing, reduce the risk of a psychiatric disorder in the fetus.

Exemplary compounds for the methods and uses described herein include agents or compounds that inhibit Th17 activity, including: inhibitors of RORγt activity and/or IL-17 activity. Exemplary inhibitors of RORγt activity include: TMP778 (Skepner et al. 2014, J Immunol 192:2564-2575), SR1001 (Solt et al. 2011, Nature 472:491), SR1555 (Solt et al. 2012, ACS Chem Biol 7:1515), and SR2211 (Kumar et al. 2012, ACS Chem Biol 7:672). These and other inhibitors of RORγt activity, as well as assays for detecting/assessing RORγt activity, are described in, for example, U.S Patent Application Publication Nos. 2014/0275490, 2013/0085162, 2013/0065842 and 2007/0154487; U.S. Pat. No. 9,101,600; and WO2013/036912, WO2012/074547, WO2013/079223, WO2013/178362, WO2011/112263 (SR-9805), WO2011/112264, WO2010/049144, WO2012/027965, WO2012/028100, WO2012/100732, WO2012/100734, WO2011/107248, WO2012/139775, WO2012/064744, WO2012/106995, WO2012/147916, and WO2010/049144, the entire content of each of which is incorporated herein by reference. Other inhibitors of RORγt activity are also described in Skepner et al. (2014, J Immunol 192:2564-2575), Skepner et al. (2015, Immunology doi: 10.111/imm.12444, epub ahead of print), Nishiyama et al. (2014, Bioorganic & Medicinal Chemistry 22:2799-2808; compound 5b), Fauber et al. (2014, J Medicinal Chem 57:5871-5892), Liu et al. (2014 J Immunol 192:59-72), Mele et al. (2013, J Exp Med 210:2181-2190), Dhar et al. (2013, Annual Reports in Medicinal Chemistry 48:169-182), Xu et al. (2011, J Biol Chem 286:22707; ursolic acid) and Huh et al. (2011, Nature 472:486-490), the entire content of each of which is incorporated herein by reference. With respect to Fauber et al. and Dhar et al., in particular, each of the references cited therein is also incorporated herein by reference in its entirety.

Exemplary inhibitors of IL-17 activity include antibodies specific for IL-17a or the IL-17 receptor (IL-17R). In a particular embodiment, the inhibitor of IL-17 activity is a human monoclonal antibody or a humanized monoclonal antibody. Such antibodies are envisioned as being able to block IL-17R engagement by IL-17A. In a more particular embodiment, the human monoclonal antibody is brodalumab (AMG 827), which is specific for the IL-17R. In another particular embodiment, the humanized monoclonal antibody is ixekizumab (LY2439821) or secukinumab (AIN457), which are specific for IL-17A. Also envisioned for use in methods described herein are antibodies specific for the p19 subunit of IL-23 or the p40 subunit of IL-23 and IL-12. Exemplary antibodies specific for the p19 subunit of IL-23 include MK-3222 (SCH 900222), CNTO 1959, and AMG 139. Exemplary antibodies specific for the p40 subunit of IL-23 and IL-12 include Stelara (ustekinumab; CNTO 1275). Exemplary anti-IL17 monoclonal antibodies are described in, for example, Garber et al. (2012, Nature Biotechnology 30:475-477), the entire content of which is incorporated herein by reference.

Specific agents/compounds from each of the categories listed above are available commercially as follows: brodalumab (AMG 827) and AMG 139 are available from Amgen/MedImmune; ixekizumab (LY2439821) is available from Eli Lilly; secukinumab (AIN457) is available from Novartis; MK-3222 (SCH 900222) is available from Merck; CNTO 1959 and Stelara (ustekinumab; CNTO 1275) are available from Janssen Biotech (J & J).

Also envisioned for use in methods described herein are antibodies for other Th17 cell specific cytokines, such as, but not limited to IL-17f and IL-22. Antibodies and reagents specific for Th17 specific cell surface proteins, of which CCR6 is an example, are also envisioned for use in methods described herein. See also Hedrick et al. (2010, Expert Opin Ther Targets 14:911-922), the entire content of which is incorporated herein by reference). Blocking antibodies specific for IL-23 receptor (IL-23R) are also envisoned for use in methods described herein. See, for example, US 2014/0275490, which is incorporated herein in its entirety by reference.

Also envisioned herein are antibody fragments or altered/mutated antibodies, particularly those wherein the Fc domain is absent or altered/mutated such that the antibody fragment or mutated antibody can no longer bind to Fc receptors. Also encompassed herein are mutated antibodies or fragments thereof having enhanced binding for MHC Class I related receptor FcRn (Fc receptor neonatal) and/or FcγRIII. FcRn has been shown to be essential for transplacental passage of immunoglobulin G (IgG) antibodies. Methods for generating antibody fragments or mutated antibodies that can have enhanced binding for FcRn or that no longer bind to Fc receptors are described in Firan et al. (2001, Intern Immunol 13:993-1002), the entire content of which is incorporated herein by reference.

One skilled in the art can readily determine or assess the suitability of other compounds for use in the invention by screening in cellular assays of Th17 activity such as those described herein or known in the art, or in animal models of disease in which Th17 cell activity is implicated such as those described herein and elsewhere. See, for example, U.S Patent Application Publication No. 2007/0154487, the entire content of which is incorporated herein by reference.

Further to the above, an MIA rhesus monkey model has also been described. See, for example, Bauman et al. (2014, Biol Psychiatry 75:332-341), which is incorporated herein by reference in its entirety. In the rhesus monkey model, pregnant rhesus monkeys in whom MIA has been induced give birth to offspring with abnormal repetitive behaviors, communication, and social interactions. The abnormal repetitive behaviors, communication, and social interactions observed in the MIA mouse and rhesus monkey animal models of autism and ASD parallel symptoms observed in humans afflicted with these conditions. See, for example, Crawley (2012, Dialoues Clin Neurosci 14:293-305). Accordingly, both the MIA mouse model and the MIA rhesus monkey model provide suitable animal models in which to examine the effects of an activated maternal immune system on fetal development and the ramifications thereof in the offspring subsequently born. These animal models also provide suitable in vivo assays for evaluating potential therapeutics for the treatment of pregnant females carrying fetuses who are at risk for developing autism and schizophrenia.

Therefore, if appearing herein, the following terms shall have the definitions set out below.

The term "reduced risk of developing a psychiatric disorder" as used herein refers to a decrease in the risk that a subject will develop a psychiatric disorder.

The term "hyperinflammatory condition" as used herein refers to a condition in a subject wherein Th17 cell activity and potentially that of related T cells, such as, for example, CD8 and γδT cell receptor (TCR) T cells with similar RORγt-dependent cytokine programs is elevated relative to a suitable control subject. With regard to pregnant females, it is understood that Th17 cell activity is elevated relative to non-pregnant females. Accordingly, a "hyperinflammatory condition" in a pregnant female induced, for example, by environmental conditions, toxins, and/or an infection (e.g., viral, bacterial, or fungal) is compared relative to that of a pregnant female that has not been exposed to the aforementioned inducers or the like.

Pregnant females at risk for giving birth to offspring afflicted by ASD or an ASD-like condition also include pregnant females in whom serum IL-17a levels are elevated relative to other pregnant females of the same species. It has also been documented that pregnant females who have given birth to offspring afflicted with ASD or an ASD-like condition are more likely in subsequent pregnancies to give birth to offspring afflicted with ASD or an ASD-like condition. See, for example, Risch et al. (2014, Am J Psychiatry 171:1206-1213), the entire content of which is incorporated herein by reference.

The term "sample" as used herein refers to a fluid and/or tissue isolated from a subject. In a particular aspect, a sample is isolated from a pregnant female; such samples include, without limitation: whole blood, sera, amniotic fluid, and/or cerebrospinal fluid. The term sera refers to a component of blood from which blood cells and clotting factors have been removed.

"Preventing" or "prevention" refers to a decreased likelihood of acquiring a disease or disorder. The term may be used to encompass a decreased likelihood of at least 50%, at least 60%, at least 70%, at least 80%, at least 90%, at least 95%, at least 96%, at least 97%, at least 98%, or at least 99% relative to a control subject.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Therapeutically effective amount" means the amount of a compound that, when administered to a subject for treating a disease or disorder, is sufficient to effect such treatment for the disease or disorder. The term may also be applied with respect to the amount of a compound that, when administered to a subject for reducing the risk of developing a disease or disorder (e.g., autism spectrum disorder), is sufficient to effect such a reduction in the risk of developing the disease or disorder. The "therapeutically effective amount" can vary depending on the compound, the disease and its severity, and the age, weight, etc., of the subject to be treated.

The term 'treating' or 'treatment' of any disease or infection refers, in one embodiment, to ameliorating the disease or infection (i.e., arresting the disease or growth of the infectious agent or reducing the manifestation, extent or severity of at least one of the clinical symptoms thereof). In another embodiment 'treating' or 'treatment' refers to ameliorating at least one physical parameter of the disease. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

The agents and compounds and derivatives thereof of use in the invention may be prepared in pharmaceutical compositions, with a suitable carrier and at a strength effective for administration by various means to a subject in need thereof, such as a pregnant mother carrying a fetus at risk for developing autism. A variety of administrative techniques may be utilized, among them parenteral techniques such as subcutaneous, intramuscular, intrauterine, intravenous, intra-arterial, and intraperitoneal injections, catheterizations and the like. Average quantities of the agents and compounds and derivatives thereof may vary and in particular should be based upon the recommendations and prescription of a qualified physician or veterinarian.

The present invention further contemplates therapeutic compositions useful in practicing the therapeutic methods of this invention. A subject therapeutic composition includes, in admixture, a pharmaceutically acceptable excipient (carrier) and one or more of an agent, compound or derivative thereof, as described herein as an active ingredient.

The preparation of therapeutic compositions which contain agents, compounds, or derivatives thereof as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An agent, compound, or derivative thereof can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic agent, compound, or derivative thereof-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or cell modulation desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and subsequent shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

With respect to administration of agents or compositions thereof to pregnant females, use of methods described in U.S. Application No. 2015/0141350 and U.S. Pat. No. 9,173,907 are envisioned herein and the entire content of each of which documents is incorporated herein by reference.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Methods and Materials
Animals

Figure 15:
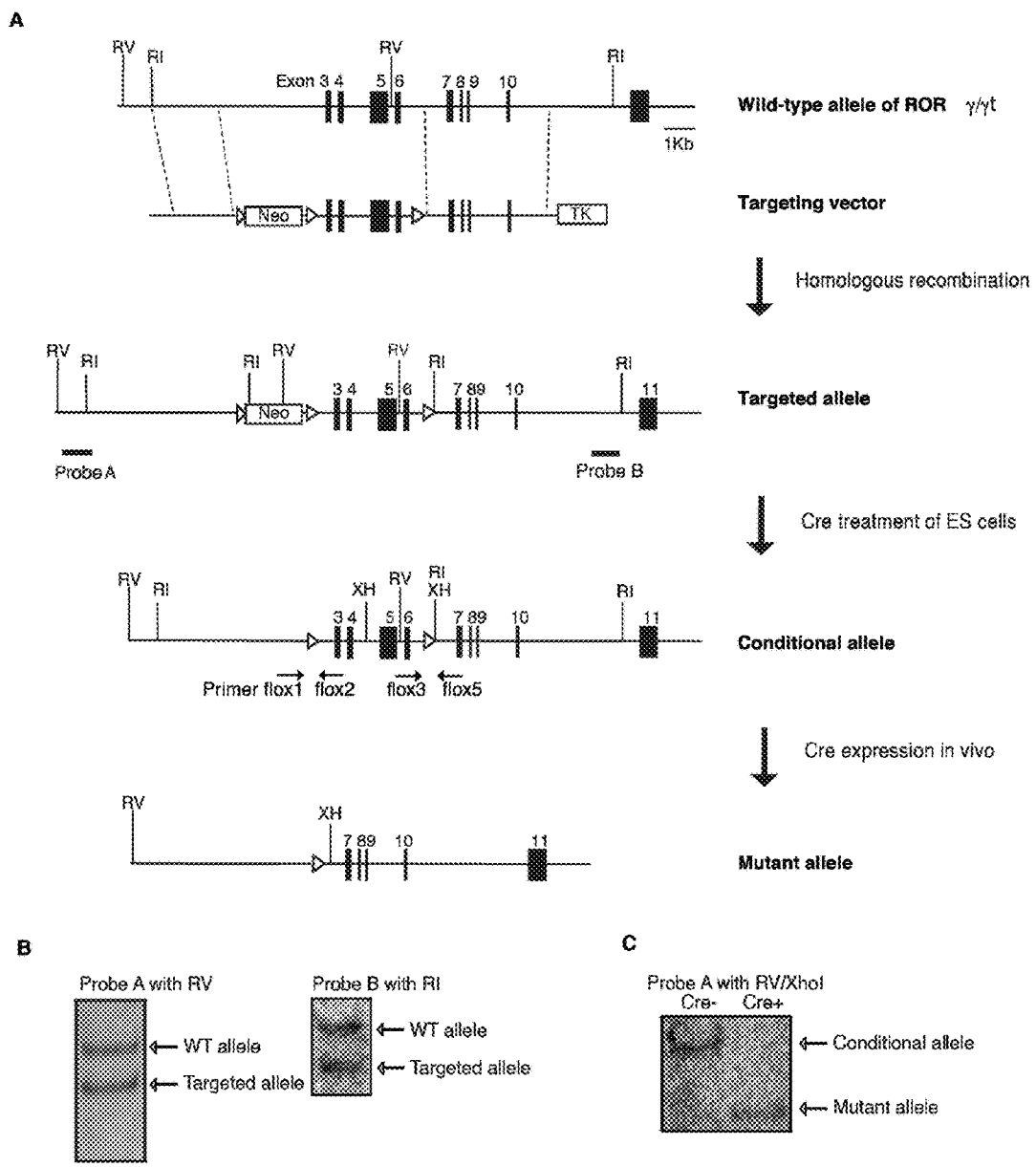
FIG. 15A-C. Generation of RORγ/γt conditional knockout mice.

All experiments were performed according to the Guide for the Care and Use of Laboratory Animals and were approved by the National Institutes of Health and the Committee and Animal Care at the New York University and University of Massachusetts. Rorc(t)$^{FL}$ mice were generated as described in FIG. 15. Rorc$^{Neo}$ mice were described elsewhere (13). C57BL/6 mice were obtained from Taconic (USA).

Generation of RORγ/γt Conditional Knockout Mice

In order to develop a conditional knockout mouse line that removes both RORγ and RORγt in a Cre-dependent manner, we generated a targeting vector, from C57BL/6-derived BAC clone RP24-318 17, in which two loxP sites flanked common exons 3-6. Cre-mediated deletion of exons 3-6 generates a frame shift mutation. Linearized targeting vector was then electroporated into albino C57BL/6 ES cells (CY2.4) in the gene targeting facility at the Rockefeller University. Homologous recombination was confirmed by Southern blot analyses with two different probes, as described in FIG. 15. To remove the neomycin resistance cassette, two ES cell lines with correctly targeted alleles were transiently electroporated with a Cre recombinase vector. ES cells with correct conditional alleles were confirmed by both Southern blot and PCR analyses and subsequently injected into blastocysts at the NYU gene targeting facility. For generating Southern blot probes, we used the following primers (ROR5Pr3s 5'-CCCAGCAGG-TAAATCAGTGGTTC-3' (SEQ ID NO: 1) and ROR5Pr3a 5'-GCGGATAGAGCAAGGTCATTGG-3' (SEQ ID NO: 2) for Probe A; ROR3Pr3s 5'-GTAACTGTGTTTATGACTC-CCTGGC-3' (SEQ ID NO: 3) and ROR3Pr3a 5'-CACTCTTTCTTGACATCTCCCCTTC-3' (SEQ ID NO: 4) for Probe B. For PCR genotyping, the following primers were used (RORgflox1 5'-TTCCTTCCTTCTTCTT-GAGCAGTC-3' (SEQ ID NO: 5), RORgflox2 5'-CA-GAAGAAAAGTATATGTGGCTTGTTG-3' (SEQ ID NO: 6) for WT 166 bps/Floxed 226 bps and RORgflox3 5'-GGT-CATTTACTGGACACCCTTTCC-3' (SEQ ID NO: 7), RORgflox5 5'-GCTACACAGCAAAACCTTGTCTTGG-3' (SEQ ID NO: 8) for WT 307 bps/Floxed 384 bps).

Maternal Immune Activation

Mice were mated overnight and females were checked daily for the presence of seminal plugs, noted as embryonic day 0.5 (E0.5). On E12.5, pregnant female mice were weighed and injected with a single dose (20 mg/kg; i.p.) of poly(I:C) (Sigma Aldrich) or PBS vehicle. Each dam was returned to its cage and left undisturbed until the birth of its litter. All pups remained with the mother until weaning on postnatal day 21 (P21), at which time mice were group housed at maximum 5 per cage with same-sex littermates. For the IL-17 cytokine blockade experiment, monoclonal IL-17a blocking antibody (clone 50104; R&D) or isotype control antibody (IgG2a, clone 54447; R&D) were administered 6 h before maternal immune activation via i.p. route (500 µg/animal). For IL-6 cytokine injection into pregnant dams, carrier-free recombinant mouse IL-6 (R&D) was administered as a single dose (10 µg/animal; i.p.). For testing anti-IL17a therapeutic effects, IL-17a blocking antibody or isotype control antibody (as described above) was administered 2 days after maternal immune activation (500 µg/animal; i.p.).

Cell Preparation, Flow Cytometry, ELISA

Embryos at each implantation site were dissected in ice-cold HBSS containing $Ca^{2+}$ and $Mg^{2+}$ (Gibco). Myometrium was first peeled off of the decidua and embryos were discarded. Dissected decidual and placental tissues were then minced and enzymatically dissociated in HBSS containing 0.28 Wunsch units (WU)/mL Liberase (Roche) and 30 µg/mL DNase I (Roche) for 30 min at 37° C. with intermittent mixing. Digested tissues were washed in PBS containing 5 mM EDTA and 5% fetal bovine serum and then incubated again in the same buffer for 15 min at 37° C. prior to filtration through a cell strainer. After separation on a discontinuous 40% & 80% Percoll gradient, the mononuclear cell fraction was treated with ACK lysis buffer (Lonza). Mononuclear cells ($1 \times 10^6$ cells/mL) were cultured for 24 h with or without phorbol 12-myristate 13-acetate (PMA, 50 ng/mL; Sigma) and ionomycin (500 ng/mL; Sigma) in T cell media: RPMI 1640 (Invitrogen) supplemented with 10% (v/v) heat-inactivated FBS (Hyclone), 50 U penicillin-streptomycin (Invitrogen), 2 mM glutamine, and 50 µM β-mercaptoethanol. Cell culture supernatant was used for ELISA analyses. Unstimulated cells were used to prepare total RNA for qPCR analyses. For flow cytometry, cells were incubated for 5 h with PMA, ionomycin and GolgiStop (BD). Intracellular cytokine staining was performed according to the manufacturer's protocol (Cytofix/Cytoperm buffer set from BD with Pacific Blue-conjugated CD4, FITC or PerCP-Cy5.5-conjugated CD8, APC-Cy7-conjugated TCR-β, PE-Cy7-conjugated anti-IL-17a, PE-conjugated anti-IFN-γ, PE-Cy7-conjugated anti-CD25 and PE-conjugated Foxp3 (eBioscience). LSR II (BD Biosciences) and FlowJo software (Tree Star) were used for flow cytometry and analysis. Dead cells were excluded using the Live/Dead fixable aqua dead cell stain kit (Invitrogen). For ELISA with sera and placenta/decidua extract, IL-6 (Ebioscience), IL-17a, TNF-α, IL-1β, IFN-β (Biolgened), and IL-10 (BD) were measured according to the manufacturer's protocol.

Ultrasonic Vocalizations

On postnatal day 7 or 9, both male and female mice were removed from the nest and habituated to the testing room for 15 minutes (separate of dam). After the habituation period, mouse pups were placed in a clean 15 cm glass pyrex high wall dish. Mouse pup ultrasonic vocalizations (USVs) were then detected for 3 min using an UltraSoundGateCM16/ CMPA microphone (AviSoft) in the sound attenuation chamber under stable temperature and light control (15 lux), and recorded with SAS Prolab software (AviSoft). USVs were measured between 33-125 kHz. USVs were scored as contiguous if gaps between vocalizations were <0.02 msec. For certain USV tests, Ultravox software (Noldus information Technology, USA) was used. An amplitude filter was used to eliminate extraneous peripheral noise (i.e. HVAC). Due to the unreliability of automated USV scoring, all pup USVs were measured and confirmed manually by observers blind to the experimental conditions.

Three-Chamber Social Approach 8-12-week-old male mice were tested for social behavior using a three-chamber social approach paradigm. Experimental mice were habituated for 1 h in separate clean holding cages and then introduced into a three-chamber arena with only empty object-containment cages (circular metallic cages, Stoelting Neuroscience) for a 10-min acclimation phase in two 5-min sessions in a 3-4 h period. The following day the mice were placed in the center chamber (without access to the left and right social test areas) and allowed to explore the center area for 5 min. After this exploration period, barriers to adjacent chambers were removed, allowing mice to explore the left and right arenas, which contained a social object (unfamiliar C57BL/6 male mouse) in one chamber and an inanimate object (plastic toy) in the other chamber. Experimental mice were given 10 min to explore both chambers and measured for approach behavior as interaction time (i.e. sniffing, approach) with targets in each chamber (within 2 cm, excluding non-nose contact or exploration). Sessions were video-recorded and object exploration time and total distance moved were analyzed using the Noldus tracking system. A social preference index was calculated as the percentage of time spent investigating the social target out of the total exploration time of both objects. The analysis was conducted with investigators blind to the treatments and genotypes of subjects. Arenas and contents were thoroughly cleaned between testing sessions. Multiple social targets from different home cages were used for testing to prevent potential odorant confounds from target home cages.

Marble Burying Test

One week following the social approach task, male mice were acclimated for 0.5-1 h in separate clean holding cages. Mice were placed in a testing arena (arena size: 16"×8"×12", bedding depth: 2") containing 20 glass marbles, which were laid out in four rows of five marbles equidistant from one another. At the end of a 15-min exploration period, mice were gently removed from the testing cages and the number of marbles buried was recorded. A marble burying index was scored as 1 for marbles covered >50% by bedding, 0.5 for ~50% covered, or 0 for anything less.

Intraventricular Cytokine Injection

At E14.5, uterine horns of pregnant mice were exposed by a caudal ventral midline incision (<2 cm). Each uterine horn was exteriorized carefully and each fetus was identified. Recombinant mouse IL-17a cytokine (R&D, 0.6 µL of 2 ng/µL), IL-6 (R&D, 0.6 µL of 10 ng/µL) or saline together with the dye Fast Green (Sigma, 0.3 mg/mL) was injected (3-4 µL) into the third ventricle of each embryo by a pulled micropipette. After injection of all embryos, the uterus was replaced within the abdomen and the cavity was lavaged with warm sterile saline.

Gender Genotyping

Genomic DNA was extracted from tail tips of each embryo. For gender discrimination of each embryo, PCR was carried out using sry (sex-determining region of the Y chromosome) gene specific primers: 5'-ACAAGTTGGC-CCAGCAGAAT-3' (SEQ ID NO: 9), and 5'-GGGATAT-CAACAGGCTGCCA-3' (SEQ ID NO: 10).

Immunohistochemistry

Fetal brains of male embryos were dissected and fixed with 4% paraformaldehyde in PBS for 6 h at 4° C. Adult brains of male offspring were perfused and fixed with 4% paraformaldehyde in PBS for overnight at 4° C. The brains were removed and sectioned at 50-µm thickness with a Leica VT1000S vibratome (Leica, USA). Slices were permeabilized with blocking solution containing 0.4% Triton X-100, 2% goat serum, and 1% BSA in PBS for 1 h at room temperature, and then incubated with anti-TBR1 (ab31940, Abcam), anti-SATB2 (ab51502, Abcam), and anti-CTIP2 (ab18465, Abcam) antibodies overnight at 4° C. The following day, slices were incubated with fluorescently conjugated secondary antibodies (Invitrogen, USA) for 1 h at room temperature, and mounted in vectashield mounting medium with DAPI (Vector laboratories). Images of stained brain slices were acquired using a confocal microscope (LSM710; Carl Zeiss) with a 20× objective lens; all image settings were kept constant. Spatial locations of the patches were registered based on their distance from the midline of the brain. These cortical malformations were quantified using cropped images containing the malformations, or the corresponding region in WT brains. The region of interest (300×300 µm$^2$) was divided into 10 equal laminar blocks representing different depths of the cortical plate. SATB2-, TBR1-, or CTIP1-positive cells were counted using Image J software. Signal intensity in each image was normalized relative to the total signal intensity.

Real-Time PCR

Total RNA was extracted from the cerebral cortex of E14.5 fetal brain of male embryo (RNase plus mini kit, Qiagen) as well as from the decidua- and the placenta-derived mononuclear cells and reverse transcribed into cDNA using oligodT (ProtoScript first strand cDNA synthesis kit, NEB) according to the manufacturer's instructions. mRNA levels of target genes (il17ra, il17rc, il17a and il16) were quantified with a Real-Time PCR System (CFX connect Real-Time PCR, Bio-Rad) using fluorescent SYBR Green technology (Bio-Rad). Real-Time PCR was performed on 2 µL of cDNA synthesized from 200 ng of total RNA. Changes in relative gene expression normalized to gapdh or actin levels were determined using the relative threshold cycle method based on the Cont-PBS group. The detailed nucleotide sequences are shown as follows:

```
                                          (SEQ ID NO: 11)
    iI117ra    5'-CCACTCTGTAGCACCCCAAT-3'
               and
                                          (SEQ ID NO: 12)
               5'-CAGGCTCCGTAGTTCCTCAG-3';

(SEQ ID NO: 13)
    il17rc     5'-GGTACTGTCCCCAGGGGTAT-3'
               and
                                          (SEQ ID NO: 14)
               5'-GAGGCCGGTTTTCATCTCCA-3';
```

-continued il17a  5'-CTCCAGAAGGCCCTCAGACTAC-3'  (SEQ ID NO: 15)
and

5'-AGCTTTCCCTCCGCATTGACACAG-3';  (SEQ ID NO: 16)

il6  5'-ACACATGTTCTCTGGGAAATCGT-3'  (SEQ ID NO: 17)
and

5'-AAGTGCATCATCGTTGTTCATACA-3';  (SEQ ID NO: 18)

actin  5'-GGCTGTATTCCCCTCCATCG-3'  (SEQ ID NO: 19)
and

5'-CCAGTTGGTAACAATGCCATGT-3';  (SEQ ID NO: 20)

gapdh  5'-AGGTCGGTGTGAACGGATTTG-3'  (SEQ ID NO: 21)
and

5'-TGTAGACCATGTAGTTGAGGTCA-3'.  (SEQ ID NO: 22)

In Situ Hybridization

E14.5 male embryos from PBS or poly(I:C)-treated mothers were collected in ice-cold PBS and subsequently fixed in 4% paraformaldehyde for 4 h at 4 Isolated brains were dehydrated in 30% sucrose/PBS solution overnight, and then embedded in Tissue Tek O.C.T. compound (Sakura Finetek, Torrance, Calif.). The blocks were sectioned at 16-μm thickness using a cryostat (Leica). Fluorescent in situ hybridization was performed using a branched cDNA probe with amplification technology (ViewRNA ISH Tissue Assay kit, Panomics, Santa Clara) according to the manufacturer's protocol. Briefly, the sections were rehydrated and treated with proteinase K for 20 min at 40° C., followed by re-fixation in 4% paraformaldehyde for 5 min. IL-17Ra and Gapdh probes were applied to the sections and incubated for 6 h at 40° C. The probes were designed based on the NCBI reference mRNA sequence: il17ra (NM_008359) and gapdh (NM_008084).

Statistics

Statistical analyses were performed using Prism or SPSS. ANOVAs were followed by Tukey or Holm-Sidak corrections. All data are represented as mean+/−SEM. Sample sizes were estimated using post-hoc power analyses from similar previously conducted studies (32, 42).

FIG. 2

USV statistics: $F(3,121)=48.55$, $p<0.0001$
Post-hoc (Tukey)
PBS,Cont-IgG vs PBS, anti-IL-17a $p=0.9878$
PBS,Cont-IgG vs Poly(I:C), Cont-IgG $p<0.0001$
PBS,Cont-IgG vs. Poly(I:C), anti-IL-17a $p=0.8899$
PBS, anti-IL-17a vs Poly(I:C), Cont-IgG $p<0.0001$
PBS, anti-IL-17a vs Poly(I:C), anti-IL-17a $p=0.6938$
Poly(I:C), Cont-IgG vs Poly(I:C), anti-IL-17a $p<0.0001$
  Social Interaction statistics: $F(3,62)=15.16$, $p<0.0001$
Social vs Inanimate (within group)
PBS,Cont-IgG; Social vs. PBS,Cont-IgG; Inanimate $p<0.0001$
PBS, anti-IL-17a; Social vs. PBS, anti-IL-17a; Inanimate $p=0.0021$
Poly(I:C), Cont-IgG; Social vs. Poly(I:C), Cont-IgG; Inanimate $p=0.1764$
Poly(I:C), anti-IL-17a; Social vs. Poly(I:C), anti-IL-17a; Inanimate $p=<0.0001$ Social Interaction across groups (between groups)
Antibody blockers $F(1,62)=10.48$, $p=0.0019$, Treatment $F(1, 62)=6.764$, $p=0.0116$,
Interaction $F(1,62)=27.59$, $p<0.0001$.
PBS,Cont-IgG vs Poly(I:C),Cont-IgG $p<0.0001$
PBS,Cont-IgG vs PBS,anti-IL17a $p=0.5241$
PBS,Cont-IgG vs Poly(I:C),anti-IL17a $p=0.967$
PBS,anti-IL-17a vs Poly(I:C),Cont-IgG $p<0.001$
Poly(I:C),Cont-IgG vs Poly(I:C); anti-IL-17a $p<0.0001$
PBS,anti-IL-17a vs Poly(I:C),anti-IL-17a $p=0.2285$
  Marble Burying statistics: $F(3,61)=62.02$, $p<0.0001$
Post-hoc (Tukey)
PBS,Cont-IgG vs PBS, anti-IL-17a $p=0.5084$
PBS,Cont-IgG vs Poly(I:C), Cont-IgG $p<0.0001$
PBS,Cont-IgG vs. Poly(I:C), anti-IL-17a $p=0.9847$
PBS, anti-IL-17a vs Poly(I:C), Cont-IgG $p<0.0001$
PBS, anti-IL-17a vs Poly(I:C), anti-IL-17a $p=0.6691$
Poly(I:C), Cont-IgG vs Poly(I:C), anti-IL-17a $p<0.0001$
  FIG. 3
  USV statistics: $F(5,97)=8.936$, $p<0.0001$
Post-hoc (Holm-Sidak)
WT (PBS) vs. WT (IC) $p<0.001$
HET (PBS) vs. HET (IC) $p<0.05$
KO (PBS) vs. KO (IC) $p=0.062$
WT (PBS) vs. HET (PBS) $p=0.538$
HET (PBS) vs. KO (PBS) $p=0.216$
KO (IC) vs. WT (IC) $p=0.012$
WT (PBS) vs. HET (IC) $p=0.002$
HET (IC) vs. KO (IC) $p=0.062$
KO (PBS) vs. WT (IC) $p<0.001$
WT (PBS) vs. KO (PBS) $p=0.852$
HET (IC) vs. KO (PBS) $p<0.001$
WT (PBS) vs. KO (IC) $p=0.248$
HET (PBS) vs. WT (IC) $p=0.001$
HET (PBS) vs. KO (IC) $p=0.876$
HET (IC) vs. WT (IC) $p=0.876$
  Social Interaction statistics: $F(5,117)=6.904$, $p<0.0001$
Social vs Inanimate (within group)
WT-PBS $p<0.0001$
WT-IC $p>0.9999$
HET-PBS $p<0.0001$
HET-IC $p>0.9999$
KO-PBS $p=0.0001$
KO-IC $p<0.0001$
Social Interaction across groups (between groups)
Genotype $F(2,117)=1.1547$, $p=0.2172$, Treatment $F(1,117)=15.27$, $p=0.0002$, Interaction $F(2,117)=4.842$, $p=0.0095$.
WT (PBS) vs. WT (IC) $p=0.0004$
HET (PBS) vs. HET (IC) $p=0.0359$
KO (PBS) vs. KO (IC) $p=0.9999$
WT (PBS) vs. HET (PBS) $p>0.9999$
HET (PBS) vs. KO (PBS) $p=0.9822$
HET (PBS) vs KO (IC) $p=0.9961$
WT(IC) vs. HET (IC) $p=0.9999$
KO (IC) vs. WT (IC) $p=0.0049$
WT (PBS) vs. HET (IC) $p=0.0139$
HET (IC) vs. KO (IC) $p=0.0714$
KO (PBS) vs. WT (IC) $p=0.0381$
WT (PBS) vs. KO (PBS) $p=0.9607$
HET (IC) vs. KO (PBS) $p=0.1929$
WT (PBS) vs. KO (IC) $p=0.9878$
HET (PBS) vs. WT (IC) $p=0.0029$
Distance moved (between groups)
Genotype $F(2,113)=0.2697$, $p=0.7641$, Treatment $F(1,113)=0.6454$, $p=0.4234$,
Interaction $F(2,113)=0.054$, $p=0.9476$.

WT (PBS) vs. WT (IC) p=0.9677
HET (PBS) vs. HET (IC) p>0.9999
KO (PBS) vs. KO (IC) p=0.9980
WT (PBS) vs. HET (PBS) p=0.9819
HET (PBS) vs. KO (PBS) p=0.9988
HET (PBS) vs KO (IC) p>0.9999
WT (IC) vs. HET (IC) p=0.9996
KO (IC) vs. WT (IC) p>0.9999
WT (PBS) vs. HET (IC) p=0.720
HET (IC) vs. KO (IC) p=0.9999
KO (PBS) vs. WT (IC) p=0.9983
WT (PBS) vs. KO (PBS) p=0.9997
HET (IC) vs. KO (PBS) p=0.9893
WT (PBS) vs. KO (IC) p=0.9722
HET (PBS) vs. WT (IC) p>0.9999

Marble Burying statistics: $F(5,114)=13.90$, $p<0.0001$, Genotype $F(2,114)=7.542$, $p<0.0001$, Treatment $F(1,114)=9.598$, $p=0.0025$, Interaction $F(2,114)=16.40$, $p<0.0001$.
Post-hoc (Tukey, corrects for multiple comparisons)
WT (PBS) vs. WT (IC) p=0.0008
HET (PBS) vs. HET (IC) p=0.0015
KO (PBS) vs. KO (IC) p=0.0507
WT (PBS) vs. HET (PBS) p=0.9996
HET (PBS) vs. KO (PBS) p=0.9388
HET (PBS) vs. KO (IC) p=0.3196
WT (IC) vs HET (IC) p=0.9963
KO (IC) vs. WT (IC) p<0.0001
WT (PBS) vs. HET (IC) p=0.0015
HET (IC) vs. KO (IC) p<0.0001
KO (PBS) vs. WT (IC) p=0.0494
WT (PBS) vs. KO (PBS) p=0.8569
HET (IC) vs. KO (PBS) p=0.0483
WT (PBS) vs. KO (IC) p=0.6361
HET (PBS) vs. WT (IC) p=0.0006

Figure 4:
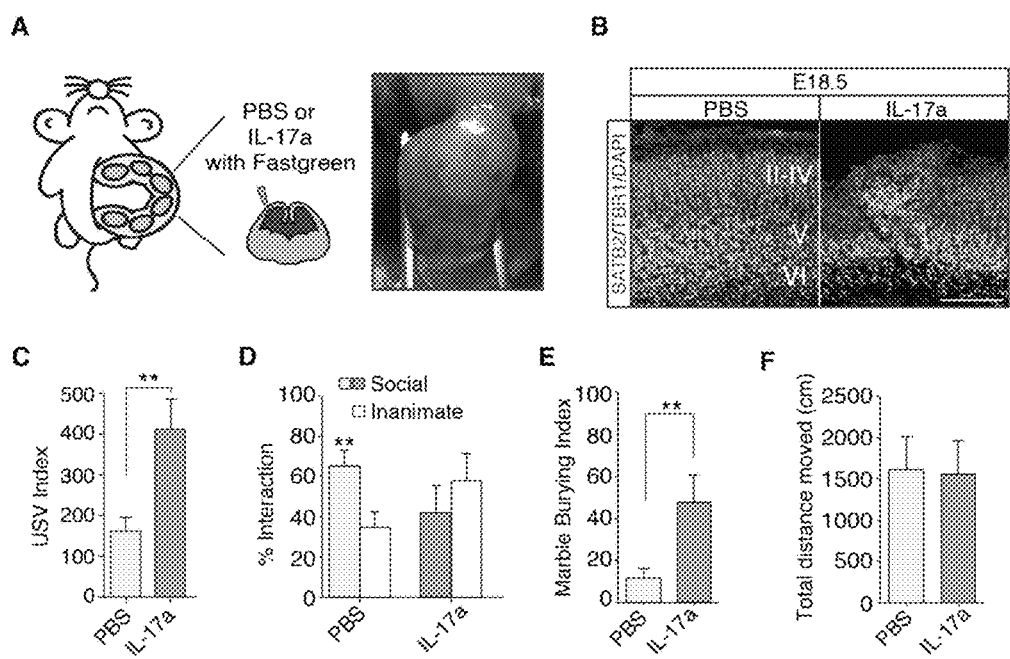
FIG. 4A-F. IL-17a administration to the fetus promotes abnormal cortical development and ASD-like behavioral phenotypes.
Figure 5:
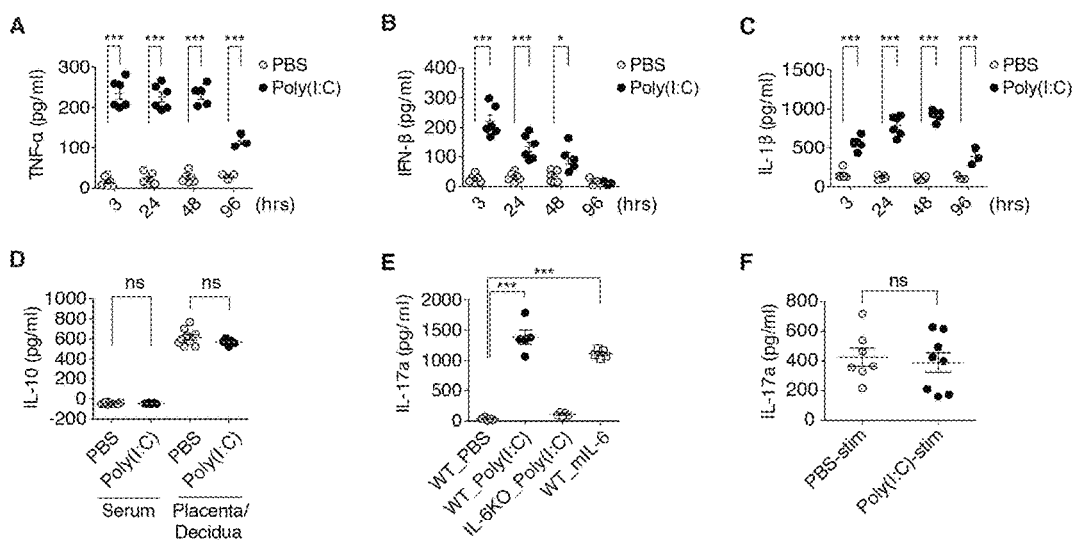
FIG. 5A-F. Expression of multiple cytokines detected upon MIA.

FIG. 4.
USV statistics: the Student's t-test
PBS vs. IL17a $p<0.0001$
Social Interaction statistics: $F(1,28)=28.65$, $p<0.0001$
Social vs Inanimate (within group)
PBS; Social vs. PBS; Inanimate p=0.0002
IL-17a; Social vs. IL-17a; Inanimate p=0.015
Marble Burying statistics: the Student's t-test
PBS vs. IL17a $p<0.0001$ FIG. 10.
Social Interaction statistics:
Social vs Inanimate (within group)
HET-PBS t(9)=3.858, p=0.004
WT-IC t(6)=0.450, p=0.669
HET-IC t(23)=3.622, p=0.001
KO-IC t(27)=8.573, p<0.001
Social Interaction (between groups)
$F(3,65)=3.544$, $p=0.019$; Genotype $F(2,68)=4.848$, $p=0.011$, Treatment $F(1,69)=2.305$, $p=0.134$,
HET (PBS) vs. WT (IC) p=0.135
HET (PBS) vs. HET (IC) p=0.433
HET (PBS) vs. KO (IC) p=0.998
WT (IC) vs. HET (IC) p=0.636
WT (IC) vs. KO (IC) p=0.042
HET (IC) vs KO (IC) p=0.113

Figure 12:
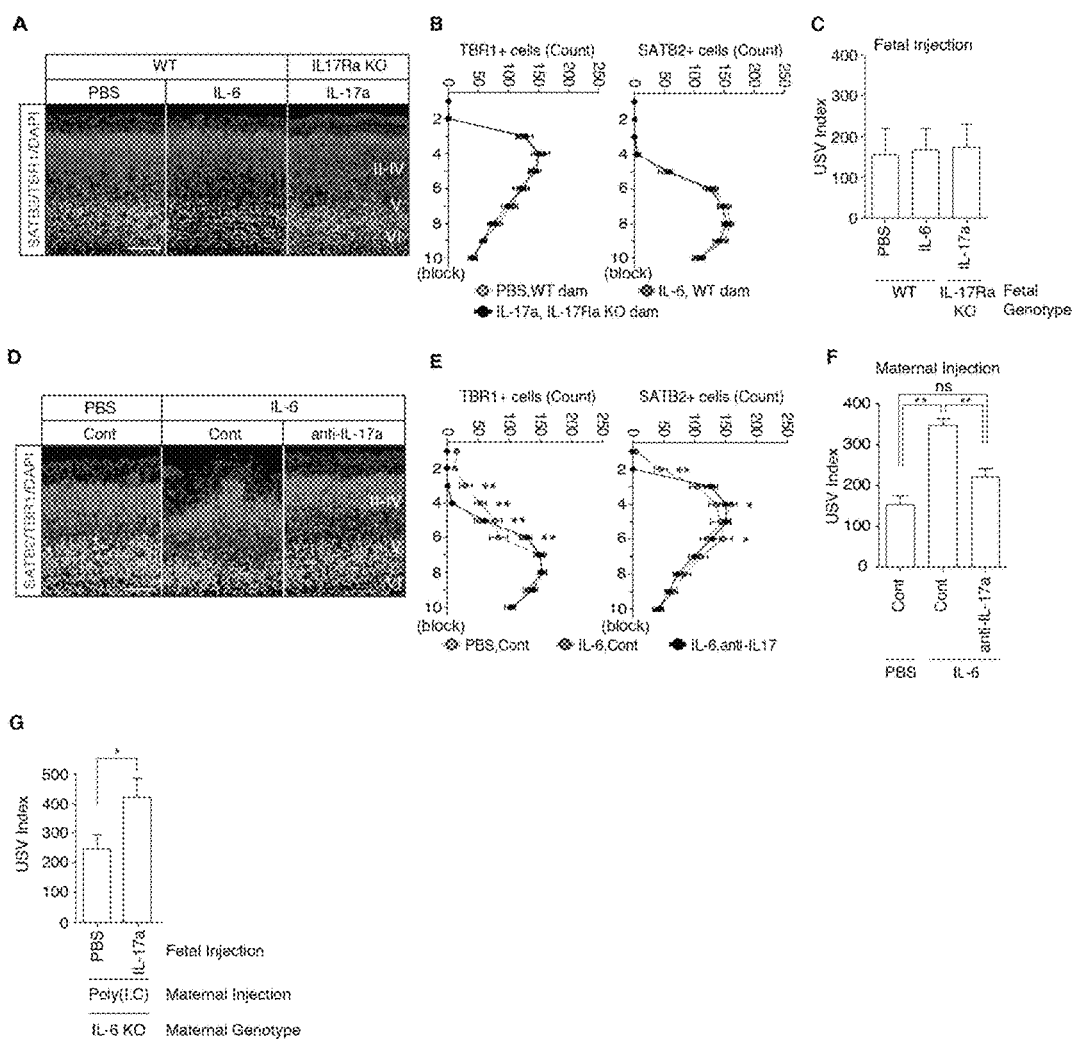
FIG. 12A-G. IL-17a acts downstream of IL-6 in the MIA.

FIG. 12.
USV statistics: the Student's t-test
PBS vs. IL17a p=0.0002
USV statistics: $F(2,44)=24.59$, $p<0.0001$
Post-hoc (Tukey)
PBS, Cont-IgG vs IL-6, Cont-IgG $p<0.0001$
PBS, Cont-IgG vs IL-6, anti-IL-17a p=0.0741
IL-6, Cont-IgG vs. IL-6, anti-IL-17a $p<0.0001$ FIG. 14.
USV statistics: $F(2,58)=97.05$, $p<0.0001$
Post-hoc (Tukey)
PBS,Cont-IgG vs Poly(I:C), Cont-IgG $p<0.0001$
PBS,Cont-IgG vs. Poly(I:C), anti-IL-17a $p<0.0001$
Poly(I:C), Cont-IgG vs Poly(I:C), anti-IL-17a $p<0.0001$
Social Interaction statistics: $F(2,36)=21.62$, $p<0.0001$
Social vs Inanimate (within group)
PBS,Cont-IgG; Social vs. PBS,Cont-IgG; Inanimate $p<0.0001$
Poly(I:C), Cont-IgG; Social vs. Poly(I:C), Cont-IgG; Inanimate p=0.0064
Poly(I:C), anti-IL-17a; Social vs. Poly(I:C), anti-IL-17a; Inanimate p=0.0255
Marble Burying statistics: $F(2,36)=120.5$, $p<0.0001$
Post-hoc (Tukey)
PBS,Cont-IgG vs Poly(I:C), Cont-IgG $p<0.0001$
PBS,Cont-IgG vs. Poly(I:C), anti-IL-17a p=0.0121
Poly(I:C), Cont-IgG vs Poly(I:C), anti-IL-17a $p<0.0001$ This invention may be embodied in other forms or carried out in other ways without departing from the spirit or essential characteristics thereof. The present disclosure is therefore to be considered as in all aspects illustrative and not restrictive, the scope of the invention being indicated by the appended Claims, and all changes which come within the meaning and range of equivalency are intended to be embraced therein.

Results

As described herein, the present inventors demonstrate that pro-inflammatory T cells expressing IL-17 cytokines are required in mothers for MIA to induce ASD-like phenotypes in affected offspring. Consistent with this observation, IL-17a blocking antibody administration in pregnant females protected against the development of MIA-induced behavioral deficits in the offspring. See, for example, FIG. 2. T cell-specific inactivation in mothers of RORγt, the transcription factor required for differentiation of T helper 17 (Th17) cells, a major source of IL-17a, similarly protected from induction of ASD-like phenotypes. See, for example, FIG. 3. Importantly, the present inventors also found abnormal cortical development in affected offspring, and this abnormality was rescued by inhibition of IL-17a signaling. See, for example, FIG. 2 and FIG. 8. IL-17a blocking antibody also conferred partial protection against the development of MIA-induced behavioral deficits in offspring when administered to pregnant mothers after MIA induction. See, for example, FIG. 14. These data suggest that therapeutic targeting of Th17 cells, major contributors to autoimmune disease, in susceptible pregnant mothers will reduce the likelihood of bearing children with inflammation-induced ASD phenotypes.

Various references are cited throughout this Specification, each of which is incorporated herein by reference in its entirety.

REFERENCES

1. H. O. Atladottir et al., Maternal infection requiring hospitalization during pregnancy and autism spectrum disorders. *J Autism Dev Disord* 40, 1423-1430 (2010).
2. P. H. Patterson, Immune involvement in schizophrenia and autism: etiology, pathology and animal models. *Behav Brain Res* 204, 313-321 (2009).
3. A. S. Brown et al., Elevated maternal C-reactive protein and autism in a national birth cohort. *Molecular psychiatry* 19, 259-264 (2014).

4. H. O. Atladottir et al., Association of family history of autoimmune diseases and autism spectrum disorders. *Pediatrics* 124, 687-694 (2009).

5. P. Ashwood, S. Wills, J. Van de Water, The immune response in autism: a new frontier for autism research. *Journal of leukocyte biology* 80, 1-15 (2006).

6. B. K. Lee et al., Maternal hospitalization with infection during pregnancy and risk of autism spectrum disorders. *Brain Behav Immun* 44, 100-105 (2015).

7. S. E. P. Smith, J. Li, K. Garbett, K. Mimics, P. H. Patterson, in *The Journal of neuroscience: the official journal of the Society for Neuroscience*. (2007), vol. 27, pp. 10695-10702.

8. N. V. Malkova, C. Z. Yu, E. Y. Hsiao, M. J. Moore, P. H. Patterson, Maternal immune activation yields offspring displaying mouse versions of the three core symptoms of autism. *Brain Behav Immun* 26, 607-616 (2012).

9. C. M. Wilke, K. Bishop, D. Fox, W. Zou, Deciphering the role of Th17 cells in human disease. *Trends Immunol* 32, 603-611 (2011).

10. N. Manel, D. Unutmaz, D. R. Littman, The differentiation of human T(H)-17 cells requires transforming growth factor-beta and induction of the nuclear receptor RORgammat. *Nat Immunol* 9, 641-649 (2008).

11. H. Spits, J. P. Di Santo, The expanding family of innate lymphoid cells: regulators and effectors of immunity and tissue remodeling. *Nat Immunol* 12, 21-27 (2011).

12. M. Lochner et al., In vivo equilibrium of proinflammatory IL-17+ and regulatory IL-10+ Foxp3+ RORgamma t+ T cells. *J Exp Med* 205, 1381-1393 (2008).

13. I. Ivanov et al., in *Cell*. (2006), vol. 126, pp. 1121-1133.

14. L. Y. Al-Ayadhi, G. A. Mostafa, Elevated serum levels of interleukin-17A in children with autism. *J Neuroinflammation* 9, 158 (2012).

15. K. Suzuki et al., Plasma cytokine profiles in subjects with high-functioning autism spectrum disorders. *PLoS One* 6, e20470 (2011).

16. B. van der Zwaag et al., Gene-network analysis identifies susceptibility genes related to glycobiology in autism. *PLoS One* 4, e5324 (2009).

17. M. Mandal, A. C. Marzouk, R. Donnelly, N. M. Ponzio, in *Journal of reproductive immunology*. (2010), vol. 87, pp. 97-100.

18. E. Y. Hsiao, S. W. McBride, J. Chow, S. K. Mazmanian, P. H. Patterson, Modeling an autism risk factor in mice leads to permanent immune dysregulation. *Proc Natl Acad Sci USA* 109, 12776-12781 (2012).

19. V. K. Kuchroo, A. Awasthi, Emerging new roles of Th17 cells. *European journal of immunology* 42, 2211-2214 (2012).

20. C. Dehay, H. Kennedy, Cell-cycle control and cortical development. *Nature reviews. Neuroscience* 8, 438-450 (2007).

21. M. F. Casanova et al., Focal cortical dysplasias in autism spectrum disorders. *Acta neuropathologica communications* 1, 67 (2013).

22. R. Stoner et al., Patches of disorganization in the neocortex of children with autism. *The New England journal of medicine* 370, 1209-1219 (2014).

23. J. De Miranda et al., Induction of Toll-like receptor 3-mediated immunity during gestation inhibits cortical neurogenesis and causes behavioral disturbances. *mBio* 1, (2010).

24. S. E. Smith, R. M. Elliott, M. P. Anderson, Maternal immune activation increases neonatal mouse cortex thickness and cell density. *Journal of neuroimmune pharmacology: the official journal of the Society on NeuroImmune Pharmacology* 7, 529-532 (2012).

25. B. J. Molyneaux, P. Arlotta, J. R. Menezes, J. D. Macklis, Neuronal subtype specification in the cerebral cortex. *Nature reviews. Neuroscience* 8, 427-437 (2007).

26. E. A. Alcamo et al., Satb2 regulates callosal projection neuron identity in the developing cerebral cortex. *Neuron* 57, 364-377 (2008).

27. C. Englund et al., Pax6, Tbr2, and Tbr1 are expressed sequentially by radial glia, intermediate progenitor cells, and postmitotic neurons in developing neocortex. *The Journal of neuroscience: the official journal of the Society for Neuroscience* 25, 247-251 (2005).

28. M. Leid et al., CTIP1 and CTIP2 are differentially expressed during mouse embryogenesis. Gene expression patterns: *GEP* 4, 733-739 (2004).

29. J. J. Schwartzer et al., Maternal immune activation and strain specific interactions in the development of autism-like behaviors in mice. *Translational psychiatry* 3, e240 (2013).

30. N. Yee, R. K. Schwarting, E. Fuchs, M. Wohr, Increased affective ultrasonic communication during fear learning in adult male rats exposed to maternal immune activation. *Journal of psychiatric research* 46, 1199-1205 (2012).

31. E. Y. Hsiao et al., Microbiota modulate behavioral and physiological abnormalities associated with neurodevelopmental disorders. *Cell* 155, 1451-1463 (2013).

32. C. A. Hoeffer et al., Removal of FKBP12 enhances mTOR-Raptor interactions, LTP, memory, and perseverative/repetitive behavior. *Neuron* 60, 832-845 (2008).

33. H. X. Wu, L. P. Jin, B. Xu, S. S. Liang, D. J. Li, Decidual stromal cells recruit Th17 cells into decidua to promote proliferation and invasion of human trophoblast cells by secreting IL-17. *Cellular & molecular immunology* 11, 253-262 (2014).

34. A. Nakashima et al., in *American journal of reproductive immunology*. (2010), vol. 63, pp. 104-109.

35. E. A. Martinez-Garcia et al., IL-17 increased in the third trimester in healthy women with term labor. *American journal of reproductive immunology* 65, 99-103 (2011).

36. G. Eberl, D. R. Littman, Thymic origin of intestinal alphabeta T cells revealed by fate mapping of RORgammat+ cells. *Science* 305, 248-251 (2004).

37. Z. Sun et al., Requirement for RORgamma in thymocyte survival and lymphoid organ development. *Science* 288, 2369-2373 (2000).

38. J. R. Huh et al., Digoxin and its derivatives suppress TH17 cell differentiation by antagonizing RORgammat activity. *Nature* 472, 486-490 (2011).

39. Y. Iwakura, H. Ishigame, S. Saijo, S. Nakae, Functional specialization of interleukin-17 family members. *Immunity* 34, 149-162 (2011).

40. E. Y. Hsiao, P. H. Patterson, Activation of the maternal immune system induces endocrine changes in the placenta via IL-6. *Brain Behav Immun* 25, 604-615 (2011).

41. K. Chen et al., Th17 cells mediate clade-specific, serotype-independent mucosal immunity. *Immunity* 35, 997-1009 (2011).

42. C. A. Hoeffer et al., Regulator of calcineurin 1 modulates expression of innate anxiety and anxiogenic responses to selective serotonin reuptake inhibitor treatment. *The Journal of neuroscience: the official journal of the Society for Neuroscience* 33, 16930-16944 (2013).

What is claimed is:

1. A method for reducing the risk of developing autism spectrum disorder in a fetus, the method comprising administering an inhibitor of T helper 17 (Th17) cell activity to a pregnant female, wherein the inhibitor of T helper 17 (Th17) cell activity is an antibody specific for IL-17a or IL-17 receptor, and wherein the pregnant female is carrying the fetus in utero.

2. The method of claim 1, wherein the autism spectrum disorder is autism.

3. The method of claim 1, wherein the inhibitor of Th17 cell activity is administered to the female in the first, second, or third trimester of the pregnancy.

4. The method of claim 1, further comprising assaying IL-17a levels in a sample isolated from the pregnant female.

5. The method of claim 4, wherein the sample is whole blood, sera, or amniotic fluid.

6. The method of claim 1, wherein the pregnant female was or is afflicted with a hyper-inflammatory condition during the pregnancy with the fetus, wherein the hyper-inflammatory condition is associated with a viral or bacterial infection or exposure to an inflammatory or environmental toxin during the pregnancy with the fetus.

7. The method of claim 1, wherein the pregnant female has given birth to at least one offspring afflicted with a autism spectrum disorder in a previous pregnancy.

* * * * *

UNITED STATES PATENT AND TRADEMARK OFFICE
CERTIFICATE OF CORRECTION

PATENT NO. : 10,100,113 B2
APPLICATION NO. : 15/042976
DATED : October 16, 2018
INVENTOR(S) : Dan R. Littman et al.

It is certified that error appears in the above-identified patent and that said Letters Patent is hereby corrected as shown below:

In the Specification

At Column 1, Lines 16-19 replace:
"The research leading to the present invention was funded in part by NIH/NCI grant 5P30CA016087-32, NIH/NCRR grant UL1RR029893, and NIH/NCI P30 CA016087-30. The United States government has certain rights in the invention."

With:
--This invention was made with government support under grant numbers R00 DK091508 and F31 NS083277 awarded by the National Institutes of Health. The government has certain rights in the invention.--

Signed and Sealed this
Twenty-first Day of May, 2019

Andrei Iancu
*Director of the United States Patent and Trademark Office*

SEQUENCE LISTING

<160> NUMBER OF SEQ ID NOS: 22

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1
cccagcaggt aaatcagtgg ttc                                              23

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
gcggatagag caaggtcatt gg                                               22

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3
gtaactgtgt ttatgactcc ctggc                                            25

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
cactctttct tgacatctcc ccttc                                            25

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
ttccttcctt cttcttgagc agtc                                             24

<210> SEQ ID NO 6
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 6
cagaagaaaa gtatatgtgg cttgttg                                          27

<210> SEQ ID NO 7
<211> LENGTH: 24
<212> TYPE: DNA
<213> ORGANISM: Artificial Sequence

```
<220> FEATURE:
<223> OTHER INFORMATION: Synthetic oligonucleotide

<400> SEQUENCE: 7
ggtcatttac tggacaccct ttcc                                          24

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
gctacacagc aaaaccttgt cttgg                                         25

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
acaagttggc ccagcagaat                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gggatatcaa caggctgcca                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ccactctgta gcaccccaat                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
caggctccgt agttcctcag                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
ggtactgtcc ccaggggtat                                               20
```

-continued

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
gaggccggtt ttcatctcca                                              20

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
ctccagaagg ccctcagact ac                                           22

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
agctttccct ccgcattgac acag                                         24

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 17
acacatgttc tctgggaaat cgt                                          23

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
aagtgcatca tcgttgttca taca                                         24

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ggctgtattc ccctccatcg                                              20

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide

```
<400> SEQUENCE: 20
ccagttggta acaatgccat gt                                              22

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
aggtcggtgt gaacggattt g                                               21

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 22
tgtagaccat gtagttgagg tca                                             23
```